US010514350B2

United States Patent
Boul et al.

(10) Patent No.: US 10,514,350 B2
(45) Date of Patent: *Dec. 24, 2019

(54) WELLBORE FLUID DISCRIMINATION USING IMPEDANCE SPECTRA CHARACTERISTICS

(71) Applicant: Halliburton Energy Services, Inc., Houston, TX (US)

(72) Inventors: Peter James Boul, Houston, TX (US); Randal Thomas Beste, Katy, TX (US); Jesse Kevin Hensarling, Cleveland, TX (US); Krishna M. Ravi, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 688 days.

This patent is subject to a terminal disclaimer.

(21) Appl. No.: 15/116,752

(22) PCT Filed: Jun. 24, 2014

(86) PCT No.: PCT/US2014/043905
§ 371 (c)(1),
(2) Date: Aug. 4, 2016

(87) PCT Pub. No.: WO2015/199659
PCT Pub. Date: Dec. 30, 2015

(65) Prior Publication Data
US 2017/0131226 A1     May 11, 2017

(51) Int. Cl.
*E21B 33/14*     (2006.01)
*E21B 47/00*     (2012.01)
(Continued)

(52) U.S. Cl.
CPC ............. *G01N 27/04* (2013.01); *E21B 33/14* (2013.01); *E21B 47/0005* (2013.01);
(Continued)

(58) Field of Classification Search
CPC ...... E21B 33/13; E21B 33/14; E21B 47/0005; E21B 47/10; E21B 47/102; G01N 27/04;
(Continued)

(56) References Cited

U.S. PATENT DOCUMENTS 6,984,986 B2    1/2006    Sosnowski et al.
7,679,368 B2    3/2010    Folberth
(Continued)

FOREIGN PATENT DOCUMENTS

WO     WO-2014007878 A1    1/2014
WO     WO-2015199659 A1    12/2015

OTHER PUBLICATIONS

Perini et al., "Electrochemical impedance spectroscopy for in situ petroleum analysis and water-in-oil emulsion characterization", Aug. 5, 2011, The Science and Technology of Fuel and Energy 91, pp. 224-228.*

(Continued)

*Primary Examiner* — Daniel P Stephenson
(74) *Attorney, Agent, or Firm* — Chamberlain Hrdlicka

(57) ABSTRACT

An apparatus and method may operate to mount an electrode assembly with the exterior of a casing string to be placed in a borehole in a subterranean formation. The electrode assembly may include electrodes in spaced relation to one another. After the casing string and associated electrode assembly are in the borehole, the method may include providing a series of excitation signals at a plurality of frequencies to at least one electrode to inject a series of injection signals into fluid in the annulus. The method can further include receiving signals in response to the series of injection signals through at least one other electrode. The received signals can be representative of an impedance spectrum including impedance values representative of the fluid in the borehole annulus. The method can further
(Continued)

include identifying the fluid in reference to the impedance spectrum. Additional apparatus, systems, and methods are disclosed.

20 Claims, 17 Drawing Sheets

(51) Int. Cl.
  *E21B 47/10* (2012.01)
  *G01N 27/04* (2006.01)
  *G01N 33/38* (2006.01)
(52) U.S. Cl.
  CPC ........... *E21B 47/10* (2013.01); *G01N 27/048* (2013.01); *G01N 33/383* (2013.01)
(58) Field of Classification Search
  CPC ...... G01N 27/048; G01N 33/383; G01N 3/20; G01N 3/38
  See application file for complete search history.

(56) References Cited

U.S. PATENT DOCUMENTS

| | | | |
|---|---|---|---|
| 8,030,063 B2* | 10/2011 | Kader | A01N 1/02 422/547 |
| 8,297,352 B2 | 10/2012 | Roddy et al. | |
| 8,636,063 B2 | 1/2014 | Ravi et al. | |
| 2014/0062489 A1* | 3/2014 | Pindiprolu | G01N 13/00 324/347 |
| 2017/0131226 A1* | 5/2017 | Boul | G01V 3/20 |
| 2017/0146680 A1* | 5/2017 | Boul | G01V 3/24 |

OTHER PUBLICATIONS

"International Application Serial No. PCT/US2014/043905, International Search Report dated Apr. 13, 2015", 3 pgs.
"International Application Serial No. PCT/US2014/043905, Written Opinion dated Apr. 13, 2015", 12 pgs.
"Venezuela Application Serial No. 2015000484, Office Action dated Jun. 21, 2016".

* cited by examiner

WELLBORE FLUID DISCRIMINATION USING IMPEDANCE SPECTRA CHARACTERISTICS

This application is a U.S. National Stage Filing under 35 U.S.C. 371 from International Application No. PCT/US2014/043905, filed on Jun. 24, 2014 and published as WO 2015/199659 A1 on Dec. 30, 2015, which application and publication are incorporated herein by reference in their entirety.

BACKGROUND

Understanding the structure and properties of geological formations is important for a wide variety of applications in well and reservoir management, monitoring, and remediation. Fluid sensing devices can detect certain properties of fluids to aid in attaining this understanding. However, available fluid sensing devices typically couple to a drill string or drill string tool such as a logging-while-drilling (LWD) tool and, as such, are isolated from annular regions between a casing string and formation. Therefore, available fluid sensing devices cannot detect many conditions that would be of interest to an operator during or after cementation processes when operators place cement in the annular regions. For example, some available fluid sensing devices may incapable of monitoring sealants in the annulus before and after sealants are set.

DETAILED DESCRIPTION

To address some of the challenges described above, as well as others, apparatuses, systems, and methods are described herein for using electrode-based fluid sensing components, mounted on a casing, to detect identities or properties of fluids in an annulus between the casing and a formation.

Figure 1:
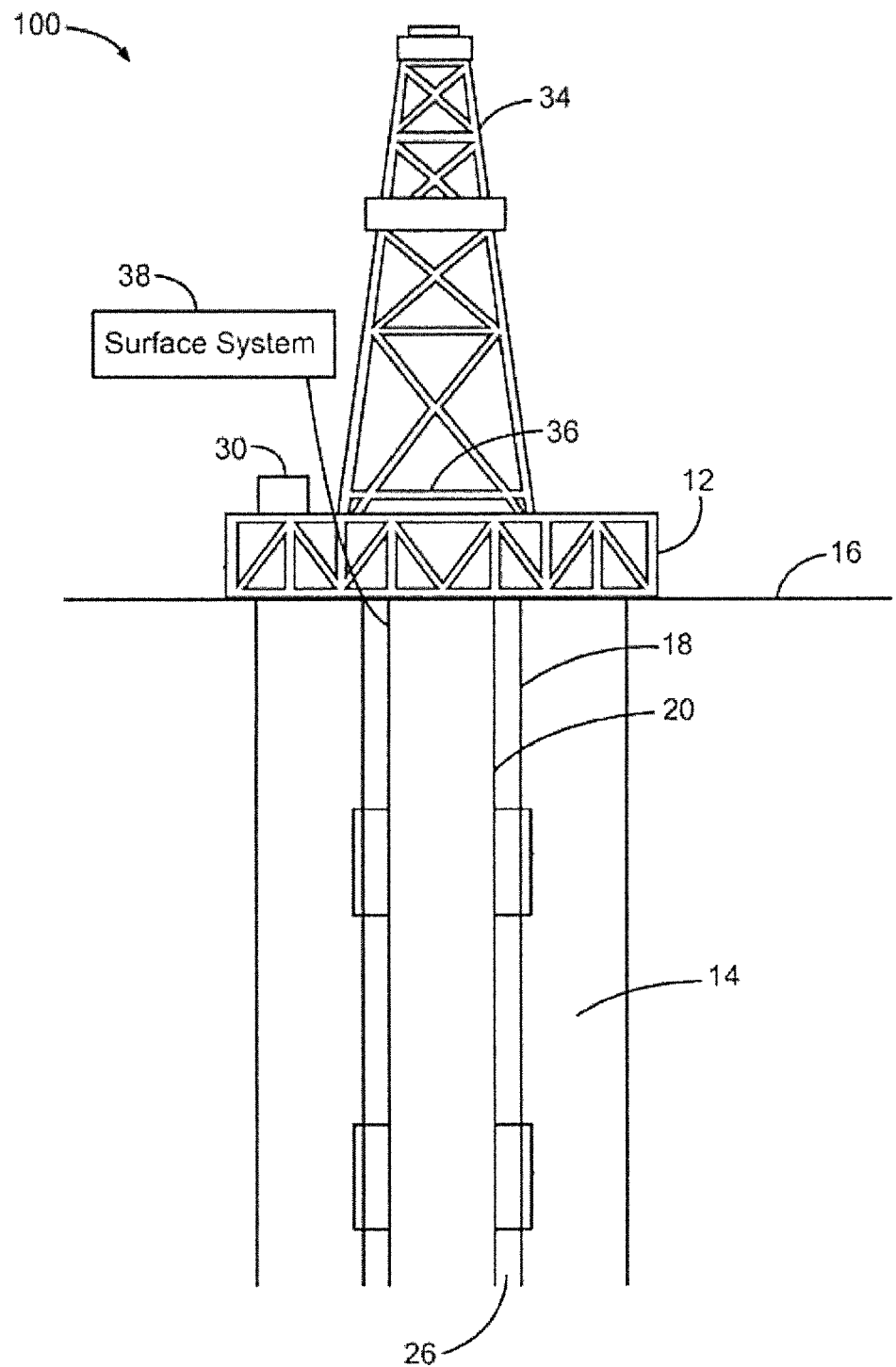
FIG. 1 illustrates a drilling system in which example embodiments can be implemented.

FIG. 1 illustrates a drilling system 100 in which example embodiments can be implemented. Drilling system 100 includes a drilling rig 12 centered over a subterranean oil or gas-bearing formation 14 located below the earth's surface 16. Rig 12 includes a derrick 34 supporting a hoisting apparatus 36 for raising and lowering pipe strings such as casing 20, and other equipment into a wellbore 18. One or more pumps 30 are arranged for pumping of a variety of wellbore fluids as may be used for various well operations (e.g., drilling mud, well control fluids, and cement or other sealants, etc.).

Wellbore 18 has been drilled through the various earth strata, including formation 14. While wellbore 18 is shown as being drilled vertically, wellbore 18 can also be drilled horizontally. During well completion, casing 20 is placed in wellbore 18 to stabilize the well and to facilitate the production of oil and gas from formation 14. Casing 20 together with the formation sidewalls defining wellbore 18 define an annulus 26 surrounding casing 20.

Drilling mud or other fluids can initially be in place in annulus 26 to maintain pressure control of the well. "Cement" or another form of sealant is used to secure casing 20 in place and to isolate the formations penetrated by wellbore 18 from one another. In an example cementation process, cement slurry is pumped down the inside of casing 20. As the cement slurry reaches the bottom of casing 20, the cement slurry flows out of casing 20 and up through the annulus, displacing any fluid such as drilling mud in annulus 26. During spotting of the cement slurry, the cement can become contaminated with drilling mud or other fluids, and this contamination can have a negative impact on the curing and integrity of the cement.

In various example systems, different structure and methodologies use alternating current (AC) impedance spectroscopy (IS) to diagnose and to assess the health of the cement after placement. AC impedance sensors, when placed downhole, offer real-time feedback of the composition and integrity of the placed cement. As the placed cement cures, chemical reactions and changes in cement structure result in changes in measured impedance sensed by AC impedance sensors. Communication circuitry downhole transmits measured impedance values to a central processing unit, for example surface system 38, located at the wellhead. Surface system 38 or another processor can monitor the cure state and quality of cement in response to the changes in impedance measurements by comparing impedance measurements against sets of measurements that were previously captured in a laboratory or other environment.

Further, surface system 38 or another processor can perform fluid identification through impedance measurements. For example, the surface system 38 can identify drilling mud, spacer fluids, and other fluids, and the surface system 38 can distinguish these and other fluids from cement through examination of impedance spectra. Additionally, methods described later herein can distinguish uncontaminated cement from cement that has been contaminated by either drilling mud or spacer fluid.

Systems and Methods for Generating Impedance Spectra

In accordance with various embodiments, operators can conduct laboratory measurements to describe cement and other fluids according to impedance properties of the cement and other fluids. Surface system 38 can store data, such as AC spectroscopic impedance signatures, in remote or local data storage. Surface system 38 can retrieve and examine the saved data to determine properties of cement during the time that the cement is monitored by other sensors, described in more detail below, located on casing 20 within wellbore 18.

Figure 2:
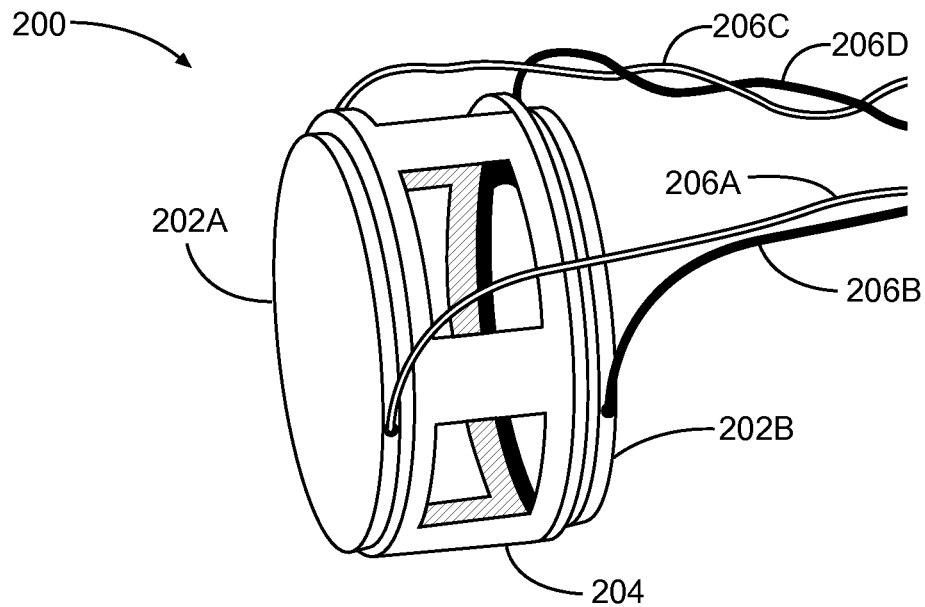
FIG. 2 depicts an example electrode system for use in an impedance measurement system for describing cement prior to pumping cement into a well.

FIG. 2 depicts an example electrode system 200 for use in an impedance measurement system (300 in FIG. 3) for describing cement prior to pumping cement into a well. By way of non-limiting example, the electrode system 200 can include two electrodes 202A and 202B. Electrodes 202A-B can be in the shape of discs although embodiments are not limited thereto. Electrodes 202A-B can include a metal such as stainless steel, and electrodes 202A-B can have dimensions including about a 2-inch diameter.

Electrodes 202A-B will attach to a spacer 204. Spacer 204, which can be manufactured through a variety of methods including 3-D printing, can separate electrodes 202A-B by about ½" such that the polished surfaces of electrodes 202A-B face each other. Spacer 204 can be printed with an acrylonitrile/butadiene/styrene (ABS) polymer in some embodiments. However, the material included in the spacer and its method of manufacture can include other materials based on criteria including cost, or on durability with respect to temperature, pressure, or chemical environments.

Wires electrically couple to electrodes 202A-B. In some embodiments, four wires 206A, 206B, 206C, and 206D are used. Wires 206A-D can be 24 American wire gauge (AWG) wires, and can be soldered with high melting point (HMP) solder onto electrodes 202A-B, although embodiments are not limited to any particular gauge or solder.

Figure 3:
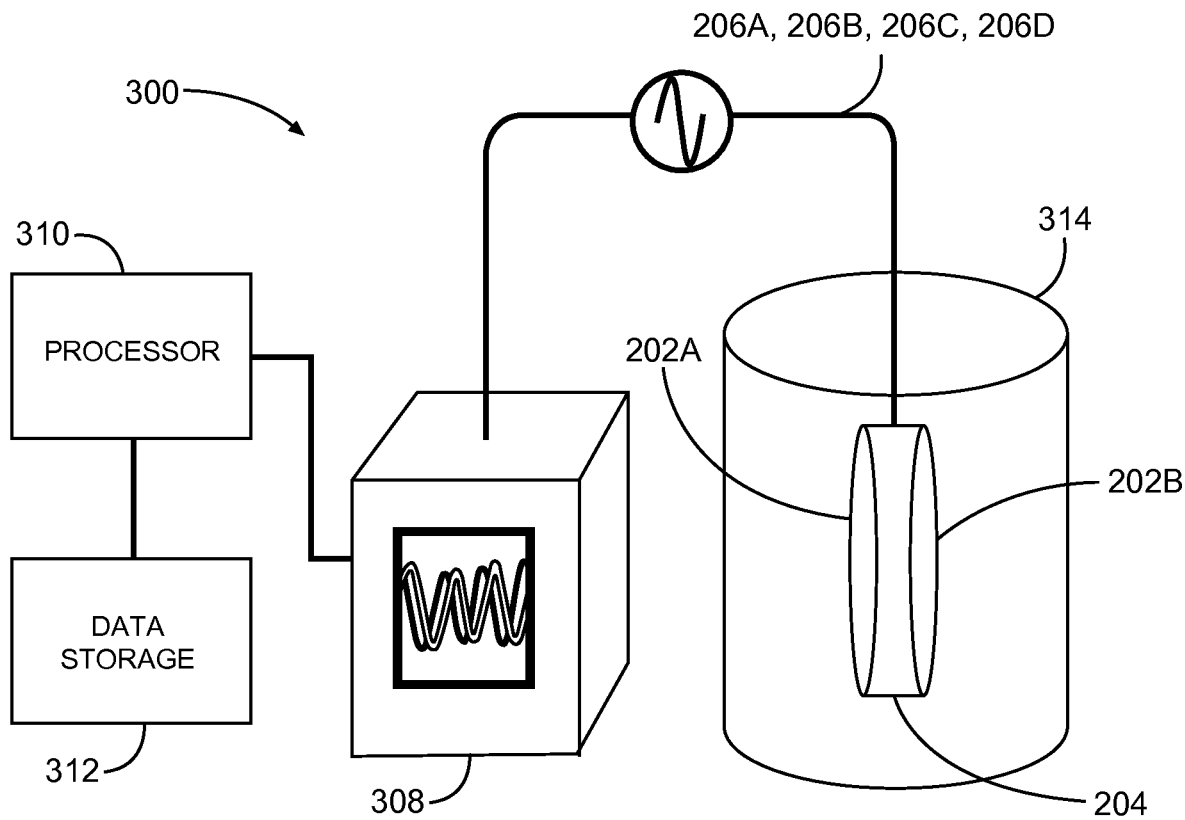
FIG. 3 depicts an impedance measurement system for measurement of impedance values of a fluid in accordance with some embodiments.

FIG. 3 depicts an impedance measurement system 300 for measurement of impedance values of a fluid in accordance with some embodiments. Components comparable to those discussed relative to FIG. 2 are numbered similarly in FIG. 3. The impedance measurement system 300 will use an impedance analyzer 308 (such as an Agilent 4294A impedance analyzer available from Agilent Technologies of Santa Clara, Calif.) to measure impedances of cement or other fluids prior to cement emplacement in wellbore 18, for example in an operator laboratory or other facility.

Figure 4A:
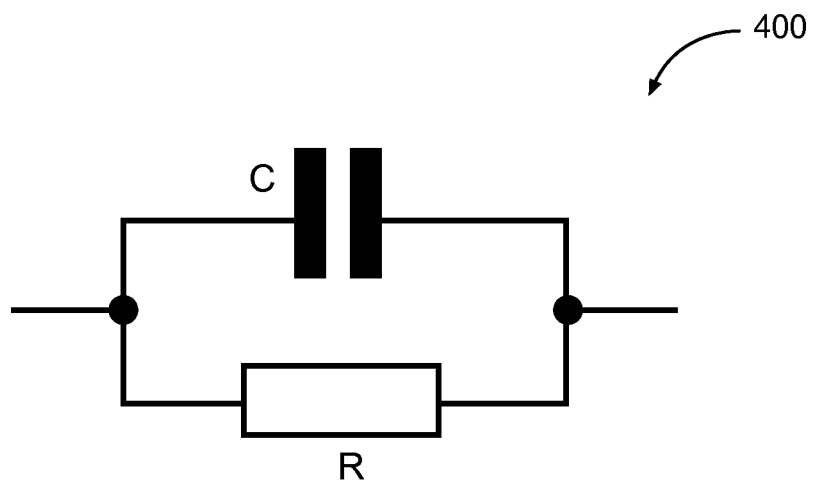
FIG. 4A depicts a model circuit that can represent impedance of an electrode-cement interface.

The resistance and capacitance of bulk cement and electrode contacts can be described with reference to equivalent circuit models of FIGS. 4A-B. Referring first to FIG. 4A, the impedances of bulk cement and electrode contacts are modeled as a parallel RC component 400. This modeling signifies that that the interface between the electrodes (202A-B in FIGS. 2 and 3) and the cement acts as a capacitor (e.g., a "contact capacitor"), in parallel with a resistor when an impedance analyzer (308 in FIG. 3) makes an impedance measurement. The contact capacitance will typically be very small, in the range of nano-farads (nF) or less, to overlap with the capacitance value resulting in the high frequency arc, described in more detail below regarding FIGS. 5A-5B, for hydrating cement systems. Therefore, the existence of the contact capacitor will be reflected in the impedance spectra in the high frequency range. However, if the contact capacitance is larger, for example in the micro-farad range, signifying a larger contact area, the influence of the contact capacitance is not detected in the high frequency range.

Figure 4B:
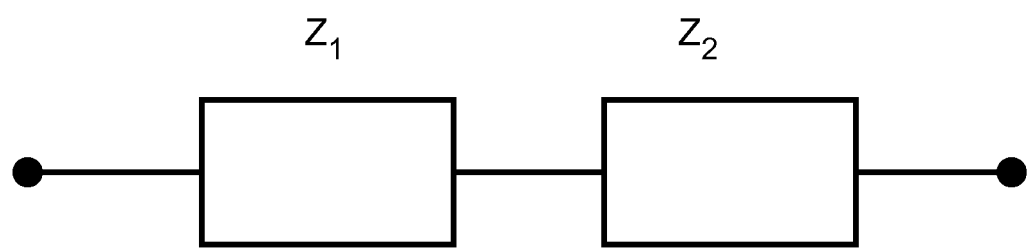
FIG. 4B depicts a model circuit that can represent impedances of bulk cement and electrode contacts.

Taken together, the resistance and capacitance of bulk cement and of the electrode contacts can be modeled as two impedances $Z_1$ and $Z_2$ in series as shown in FIG. 4B.

Referring again to FIG. 3, in embodiments, a signal generator applies an AC signal, at a range of frequencies, to electrodes 202A-B so that the AC signal passes through whatever cement or other fluids have been placed in container 314 with electrodes 202A-B. The signal generator can be incorporated in the impedance analyzer 308 or the signal generator can be separate from impedance analyzer 308. Wires 206A-D attach to impedance analyzer 308 to allow impedance analyzer 308 to capture four-point measurements of the impedance profile of the materials in the container 314 to which electrodes 202A-B were exposed. The impedance analyzer 308 or other sensor (not shown in FIG. 3) will determine current I through the materials in container 314, the potential difference V across the materials between two points, and the phase angle θ, all of which can be expressed according to Equations (1)-(2):

$$I = |I| e^{j\omega t} \qquad (1)$$

$$V = |V| e^{j(\omega t + \theta)} \qquad (2)$$

where ω is the angular frequency of the AC signal provided to electrodes 202A-B. |I| is typically a constant for a given cement specimen, |V| is sensed by sensors for sensing electrical potential, either incorporated in impedance analyzer 308 or separate sensors. Impedance analyzer 308 determines θ through comparison of the signal sensed by the potential sensors with the signal generated by the signal generator.

Real and imaginary components of impedance Z can be obtained according to Equations (3) and (4):

$$\text{Re}(Z) = \frac{|V|}{|I|}\cos\theta \tag{3}$$

$$\text{Im}(Z) = \frac{|V|}{|I|}\sin\theta \tag{4}$$

The processor 310, which can be local to the surface system 38 (FIG. 1), or remote from the surface system 38, will capture the four-point measurements of the impedance profiles and store at least some measurements in local or remote data storage 312.

In some embodiments, a system such as surface system 38 can analyze impedance data, captured using impedance analyzer 308, by analyzing Nyquist plots. As will be understood by those of ordinary skill in the art, Nyquist plots can be generated in accordance with some embodiments by making impedance gain and phase angle measurements as described above over a range of frequencies, and then plotting the imaginary and real components Re(z) and Im(Z) (Equations (3)-(4)) of the measurements.

Figure 5B:
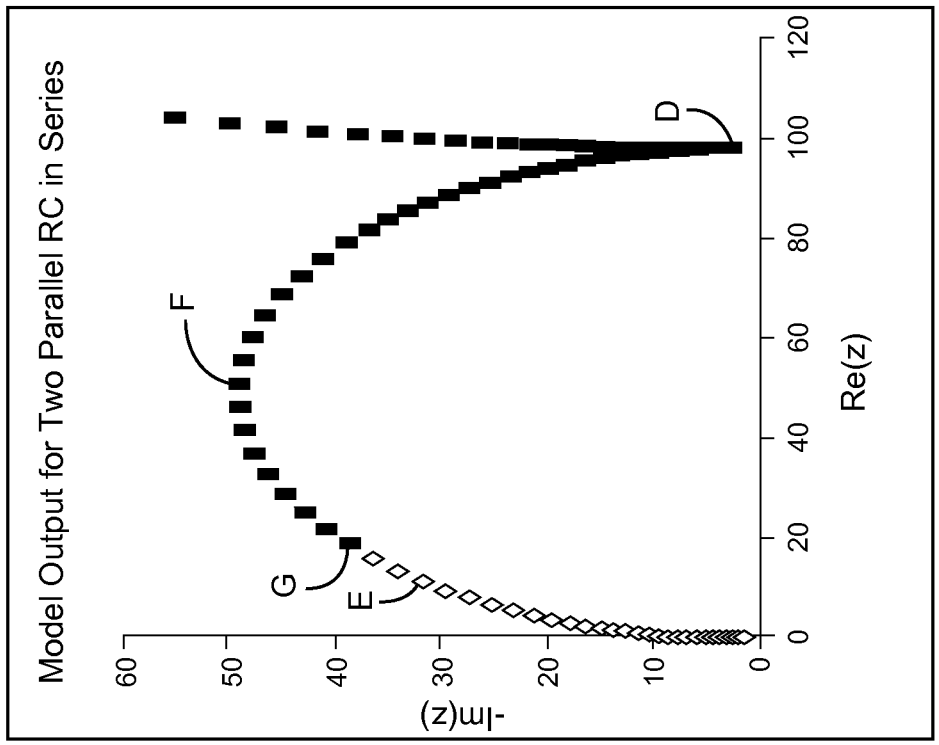
FIG. 5B illustrates a second example Nyquist plot using output impedance measurements taken using the circuit model of FIGS. 4A and 4B.
Figure 5A:
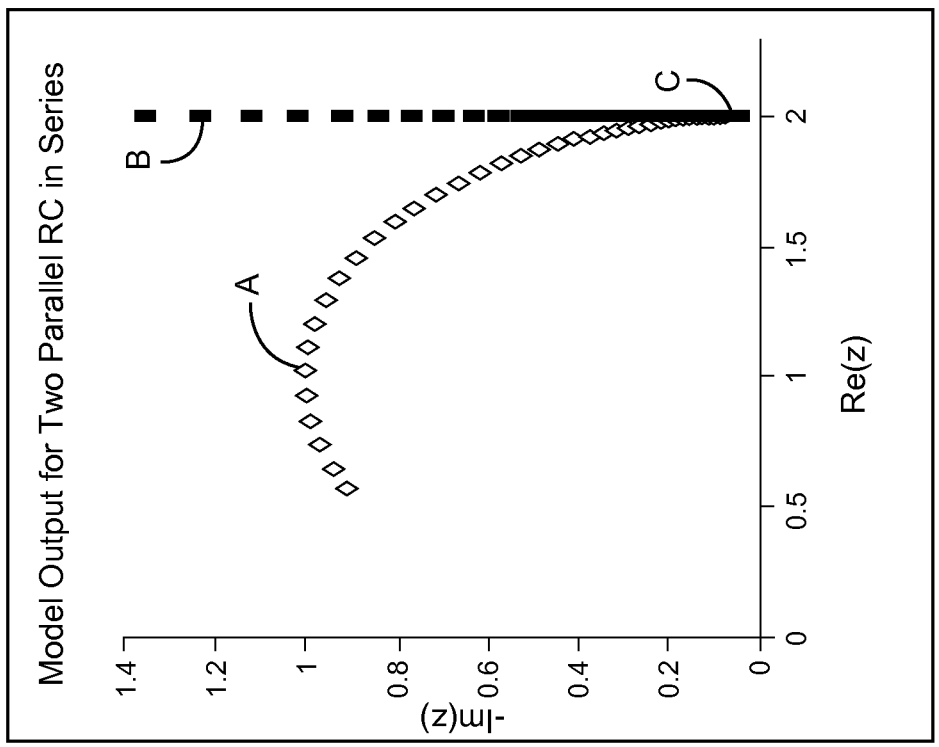
FIG. 5A illustrates a first example Nyquist plot using output impedance measurements taken using the circuit model of FIGS. 4A-B.

FIG. 5A illustrates an example Nyquist plot using output impedance measurements taken using the circuit model of FIGS. 4A-4B, when the bulk resistance of the fluid, for example cement, is equal to about 2 ohms. For example, FIG. 5A may illustrate a Nyquist plot of cement slurry, or liquid cement. The left-hand portion A is obtained by sweeping frequencies from 10 MHz to 90 MHz, and the horizontal portion B is obtained by sweeping from 290 Hz to 10 MHz. In the example of FIG. 5A with bulk resistance equal to 2 ohms, the measurement C at 10 MHz corresponds to the bulk resistance of the fluid (in this case cement slurry).

FIG. 5B illustrates a Nyquist plot using output impedance measurements taken using the circuit model of FIGS. 4A-B when the bulk resistance D of the fluid is equal to about 98 ohms. For example, FIG. 5B may illustrate a Nyquist plot of set or solidified cement. The left-hand portion of the semi-circle E on the left is obtained by sweeping frequencies from 10 MHz to 90 MHz, while the remainder F of the Nyquist plot is obtained by sweeping frequencies from 290 Hz to 10 MHz. As will be noted, the data point G taken at 10 MHz is on the bulk arc, which corresponds more to the dielectric properties of the material. This signifies that the frequency where the bulk resistance may be identified in the Nyquist plot is higher in a liquid slurry than in a set cement.

Figure 6:
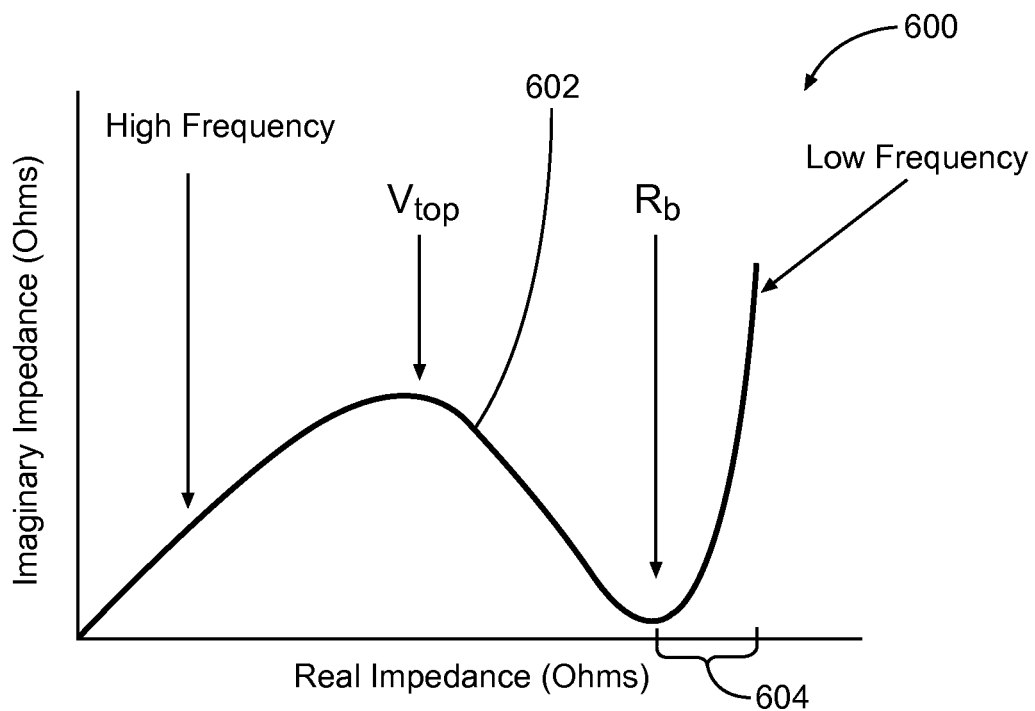
FIG. 6 illustrates a Nyquist plot using impedance measurements for cement generated in accordance with some embodiments.

FIG. 6 illustrates a Nyquist plot 600 for cement generated in accordance with some embodiments. $R_b$ is the bulk resistance of the cement. The portion 602 of the Nyquist plot can be attributed to a combination of the capacitance and the resistance of the cement. To the right of $R_b$, along the x-axis, is the RC component 604 associated with the polarization and contact resistance of electrodes 202A-B (FIG. 2). Accordingly, the portion 602 results from the bulk cement and the latter 604 from the cement-electrode interfaces. It will be appreciated that the frequency of each data point in Nyquist plot 600 decreases with increasing real impedance.

In embodiments that use AC IS, capacitive charging of the electrodes does not obscure the measurement of the bulk resistivity $R_b$. As was described earlier, this obscuring was particularly problematic for measurements of two-point DC resistivity. When Nyquist plots are generated for samples of a cement slurry as the cement slurry hydrates over time, the capacitance of the samples will be observed to change over time, and this change in capacitance can be observed through examination of the bulk arc at higher frequency. The relation of the capacitance to the resistance, and the frequency dependence thereof, renders a useful phase angle fingerprint for the fluids and solid composite materials of placed in the casing/wellbore annulus.

Figure 7:
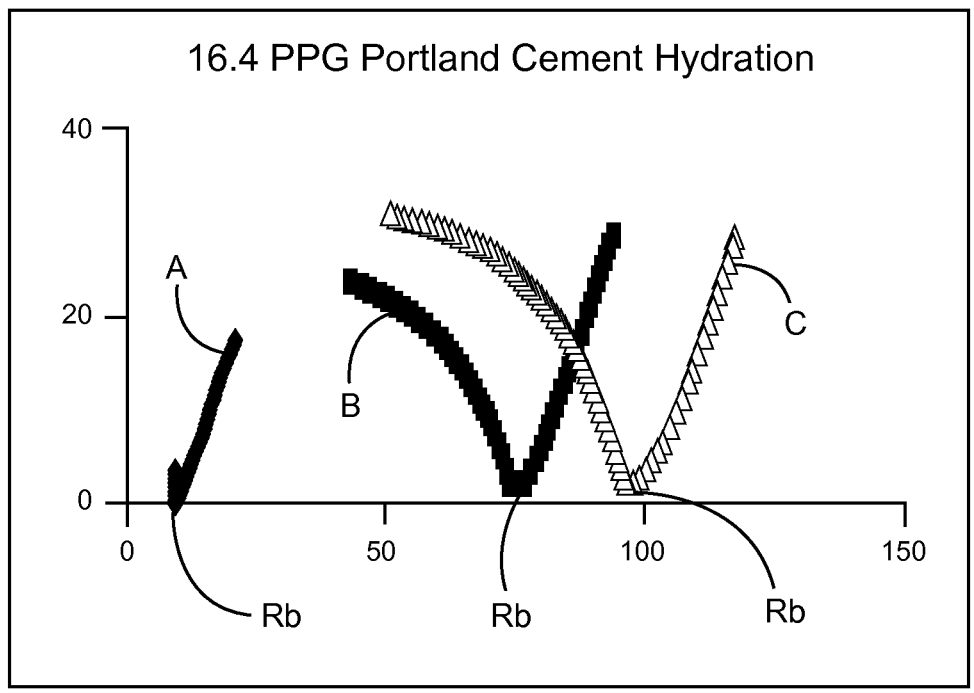
FIG. 7 depicts example impedance spectra of cement as measured at various times after cement emplacement in accordance with some embodiments.

FIG. 7 depicts example impedance spectra of cement as measured at various times after the start of cement hydration in accordance with some embodiments. Curve A represents an impedance spectrum at emplacement of the cement. Measurements of impedance in accordance with some embodiments, for example measurements of cement using an impedance measurement system 300 as described above regarding FIG. 3, indicate that the bulk resistance $R_b$ of the cement at start of cement hydration is about 10 ohms. Curve B represents an impedance spectrum 46 hours after start of cement hydration. Measurements of impedance in accordance with some embodiments indicate that the bulk resistance $R_b$ of the cement 46 hours after start of cement hydration is at about 70 ohms. Curve C represents an impedance spectrum 68 hours after the start of cement hydration. Measurements of impedance in accordance with some embodiments, indicate that the bulk resistance $R_b$ of the cement 68 hours after the start of cement hydration is at about 100 ohms. As will be appreciated upon examination of the impedance spectra of FIG. 7, the bulk resistance $R_b$ of the cement increases as the cement hydrates.

Figure 8:
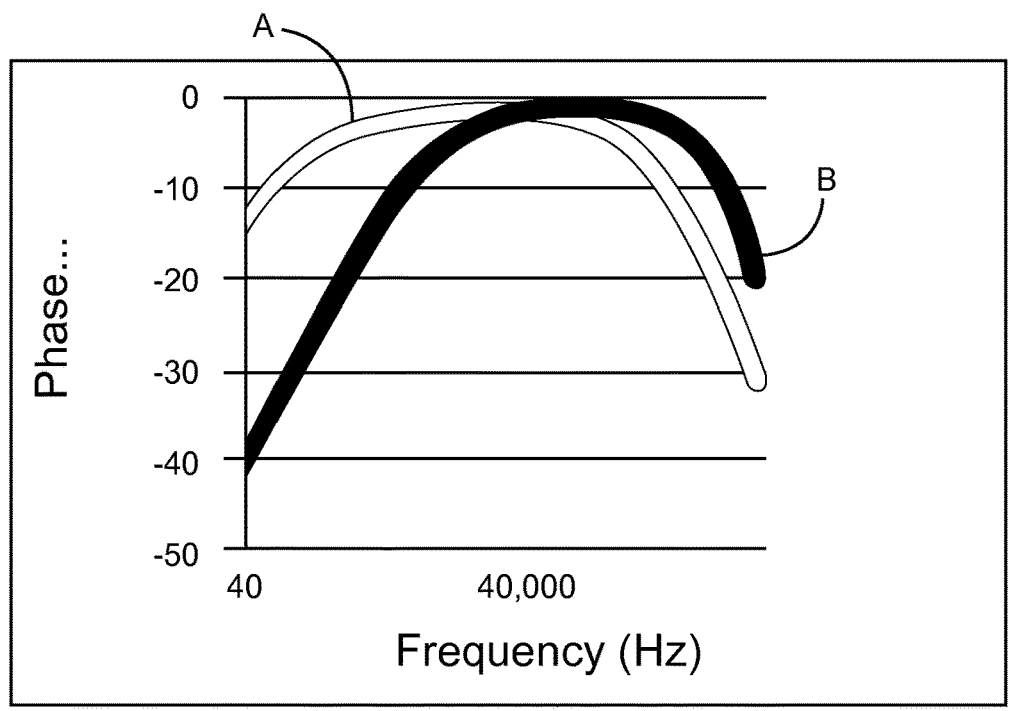
FIG. 8 illustrates example phase angle fingerprints for Portland cement prior to setting and after setting.

FIG. 8 illustrates example phase angle fingerprints for Portland cement prior to setting and after setting. As shown in FIG. 8, the phase angle ($\theta$ in equations (1)-(4) described earlier) between the sensed voltage and current signals, when graphed with respect to sweep frequency, contains a specific fingerprint for the cement slurry (curve A) and the set cement (curve B). A system, for example surface system 38 (FIG. 1) can use this phase angle fingerprint to distinguish fluids from one another. In particular, a cement slurry, set cement, tuned spacer fluid, and water-based mud will have different phase angle fingerprints when graphed relative to frequency. In order to determine whether a phase angle fingerprint matches that of a particular fluid, the system 38 can fit the phase angle fingerprint to a polynomial descriptor whereby the type of fluid is identified through a function. Values of the scalars in the function are identifiably specific to the fluid type and vary as according to the relation of reactance to real impedance as a function of alternating current frequency.

Figure 9:
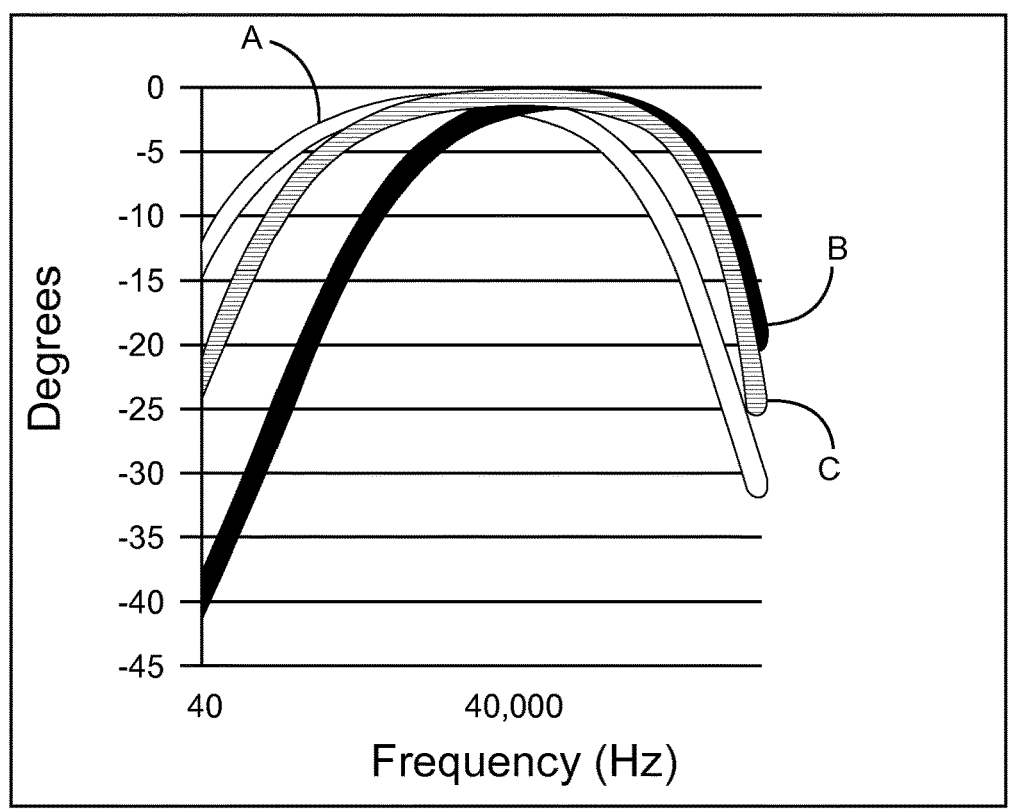
FIG. 9 illustrates example phase angle fingerprints for a tuned spacer fluid and for Portland cement prior to and after setting.

FIG. 9 illustrates example phase angle fingerprints for a tuned spacer fluid and for Portland cement prior to setting and after setting. As shown in FIG. 9, the phase angle ($\theta$ in equations (1)-(4) described earlier) between the sensed voltage and current signals, when graphed with respect to sweep frequency, contains a specific fingerprint for tuned spacer fluid (curve C) cement slurry(curve A) and the set cement (curve B). Drill mud, water-based mud, or other fluids will also have varying phase angle fingerprints. A system, for example surface system 38 (FIG. 1) can use phase angle fingerprints to distinguish fluids from one another. In particular, cement slurry, set cement, tuned spacer fluid, and water-based mud will have different phase angle fingerprints when graphed relative to frequency.

Figure 10:
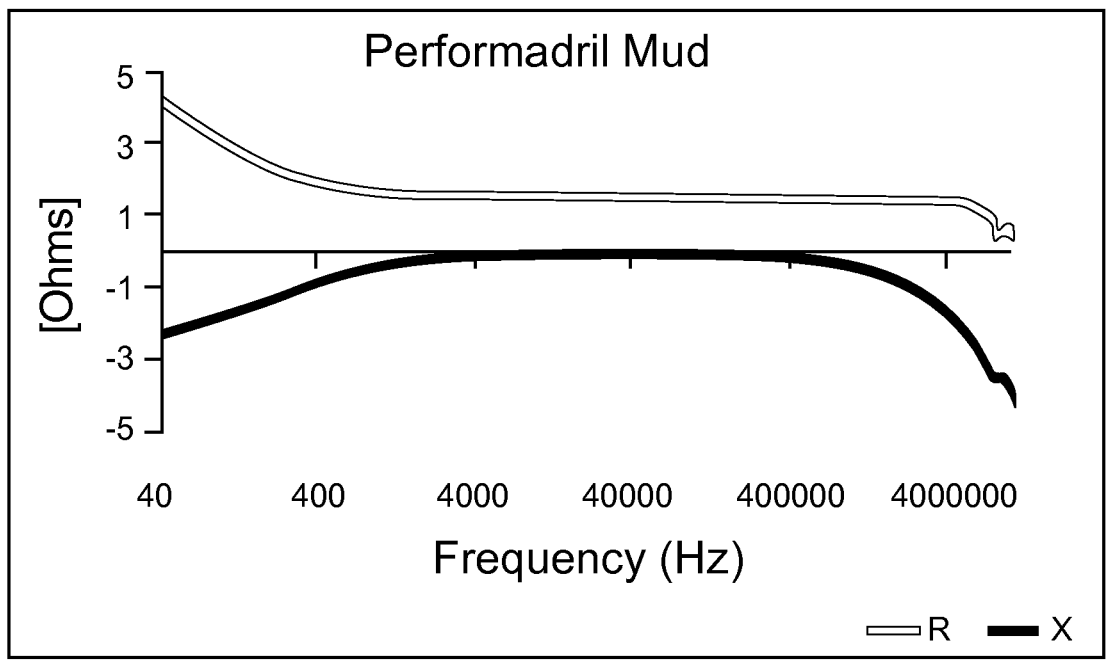
FIG. 10 illustrates reactance and resistance of a drilling mud as a function of frequency.

FIG. 10 illustrates reactance X and resistance R of a drilling mud analyzed as a function of frequency. It will be understood by those of ordinary skill in the art that FIG. 10 can also be converted into a Nyquist plot or Nyquist plots similar to those shown in FIGS. 5-7.

The example plot of FIG. 10 was created using Performadril® mud, which is available from Halliburton Company of Houston, Tex. However, similar plots or Nyquist plots, or other analysis can be performed in accordance with embodiments on any type of drilling mud or on other fluids. The example Performadril mud is a water-based drilling mud. To create the Performadril used for generating the example plot of FIG. 10, Performadril was blended at 4000 rpm in the order of (1) water, (2) sodium chloride, (3) barazan D, (4) Clayseal® Plus, which is available from Halliburton Company of Houston, Tex., (5) PAC R, and (6) Dextrid E. After the addition of Dextrid E, the remaining components (Clayseal® Plus; Performatrol®, Baroid®, and Barabuf®, all available from Halliburton Company of Houston, Tex.) were added and the slurry was blended at 12,000 rpm for 5 minutes. AC IS as described earlier herein was conducted by sweeping from 40 Hz to 5 MHz. Accordingly, the example Performadril mud that was used for generating the example plot of FIG. 10 includes the following composition. However, it will be understood that similar plots can be created for drilling mud or other fluids:

| Material | Amount (grams) | Density (g/cc) |
|---|---|---|
| Water | 276.74 | |
| NaCl | 15.04 | 2.165 |
| Barazan D Plus | 1.25 | 1.6 |
| PAC R | 1 | 1.6 |
| Dextrid E | 2 | 1.5 |
| Clayseal Plus | 3.5 | 1.0261-1.0561 |
| Performatrol | 6 | 1.03 |
| Baroid | 240.2 | 4.35 |
| Barabuf | 0.25 | |

Figure 11:
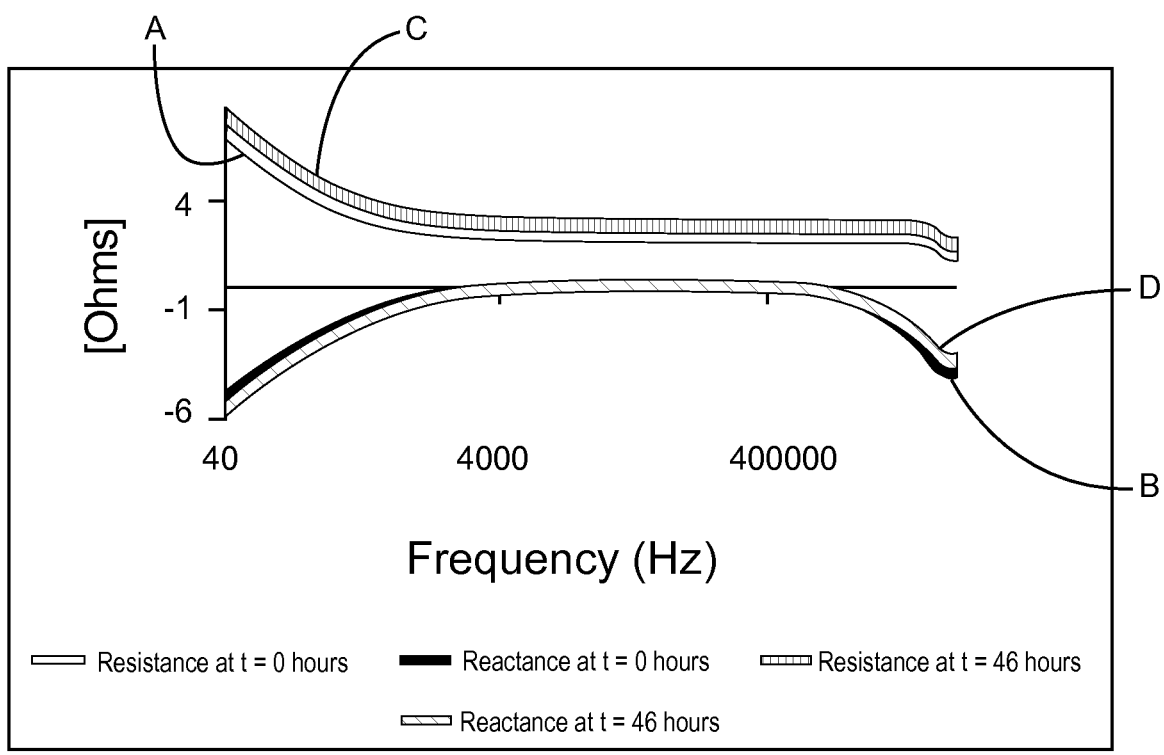
FIG. 11 illustrates a reactance and resistance diagram that further depicts time dependency of reactance and resistance when the Performadril mud contaminates cement.

FIG. 11 illustrates a reactance and resistance diagram that further depicts time dependency of reactance and resistance when the Performadril mud contaminates cement. It will be understood by those of ordinary skill in the art that FIG. 11 can also be converted into a Nyquist plot or Nyquist plots similar to those shown in FIGS. 5-7. Curve A illustrates resistance of contaminated cement at the time that Performadril mud was added as a contaminating layer, and curve B illustrates reactance of contaminated cement at the time that Performadril mud was added as a contaminating layer. Curve C illustrates resistance of contaminated cement 46 hours after the time that Performadril mud was added as a contaminating layer. Curve D illustrates reactance of contaminated cement 46 hours after the time that Performadril mud was added as a contaminating layer.

Figure 12:
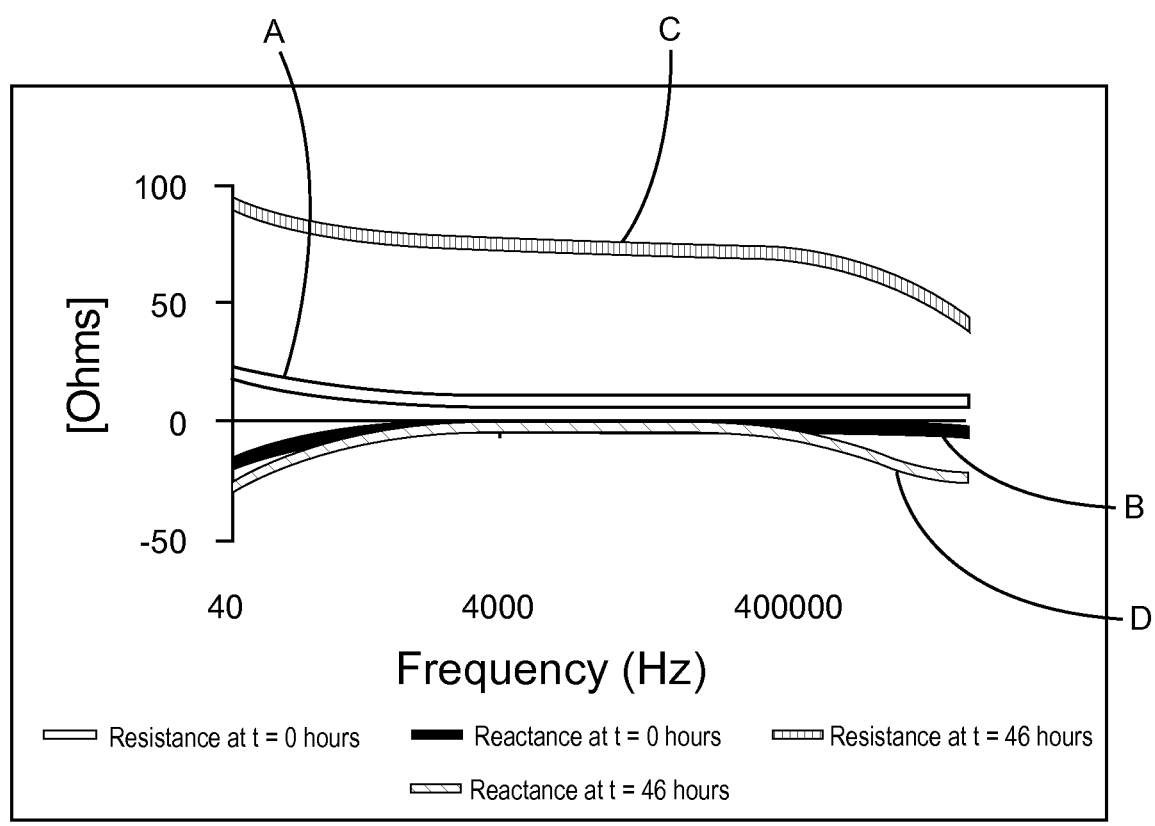
FIG. 12 illustrates an example impedance spectrum that further depicts time dependency of reactance and resistance in uncontaminated cement.

In contrast, FIG. 12 illustrates a reactance and resistance diagram that further depicts time dependency of reactance and resistance of uncontaminated cement. It will be understood by those of ordinary skill in the art that FIG. 12 can also be converted into a Nyquist plot or Nyquist plots similar to those shown in FIGS. 5-7. Curve A illustrates resistance of uncontaminated 16.4 parts per gallon (ppg) Portland cement at the start of hydration, and curve B illustrates reactance of uncontaminated 16.4 ppg Portland cement at the start of hydration. Curve C illustrates resistance of uncontaminated 16.4 ppg Portland cement 46 hours after start of hydration. Curve D illustrates reactance of uncontaminated 16.4 ppg Portland cement 46 hours after start of hydration. As will be appreciated upon comparing FIGS. 11 and 12, the curves A and C are more distinct in FIG. 12, and therefore the hydration state of uncontaminated cement is more easily determined compared to the hydration state of contaminated cement.

Figure 13:
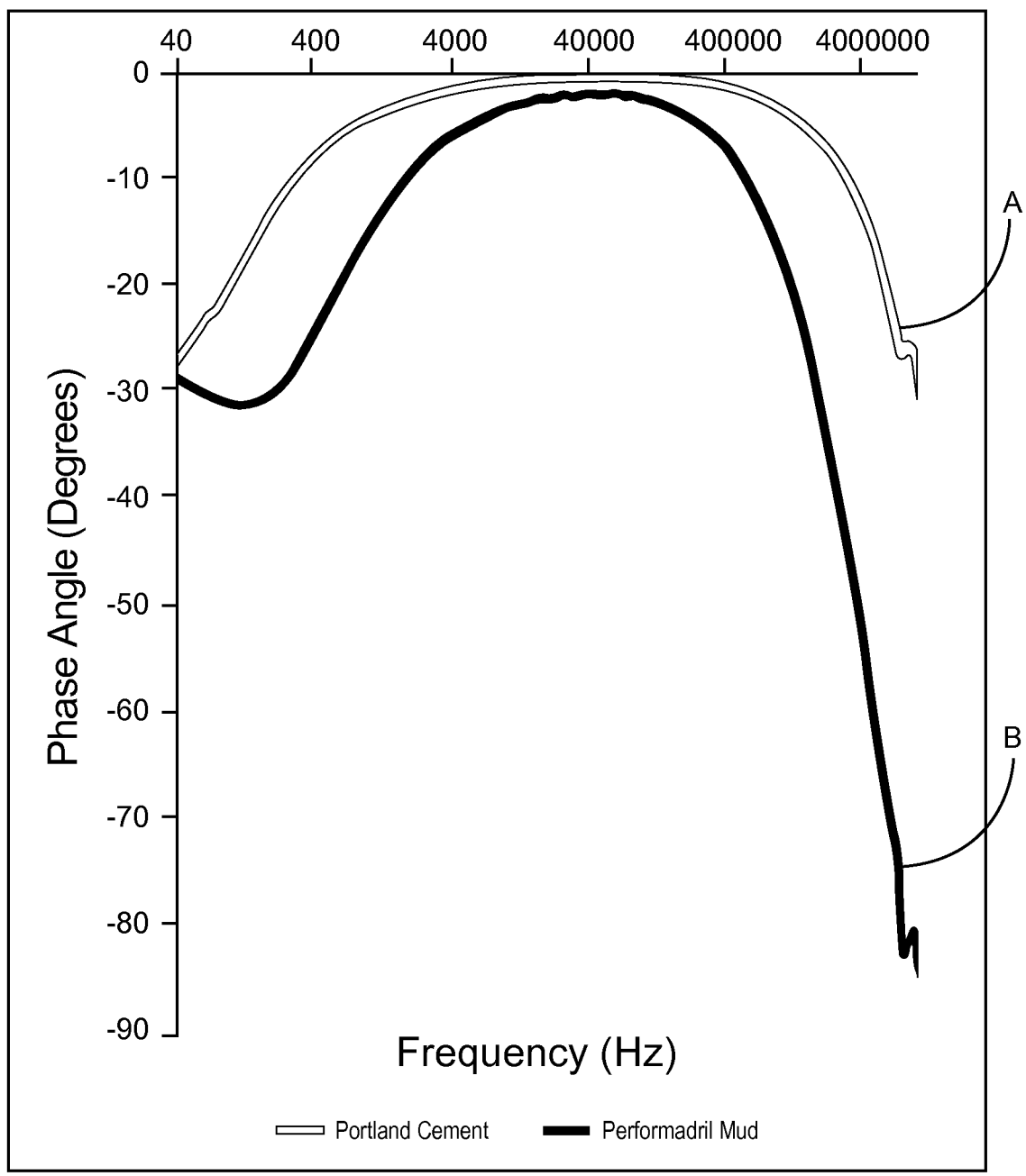
FIG. 13 illustrates example phase angle fingerprints for cement and drilling mud measured in accordance with some embodiments.

FIG. 13 illustrates example phase angle fingerprints for cement (curve A) and drilling mud (curve B) measured in accordance with some embodiments. As will be noted, the phase angle fingerprints are distinct from each other and therefore systems such as surface system 38 can distinguish mud from cement using the phase angle fingerprints measured or calculated in accordance with some embodiments described earlier herein.

Figure 14:
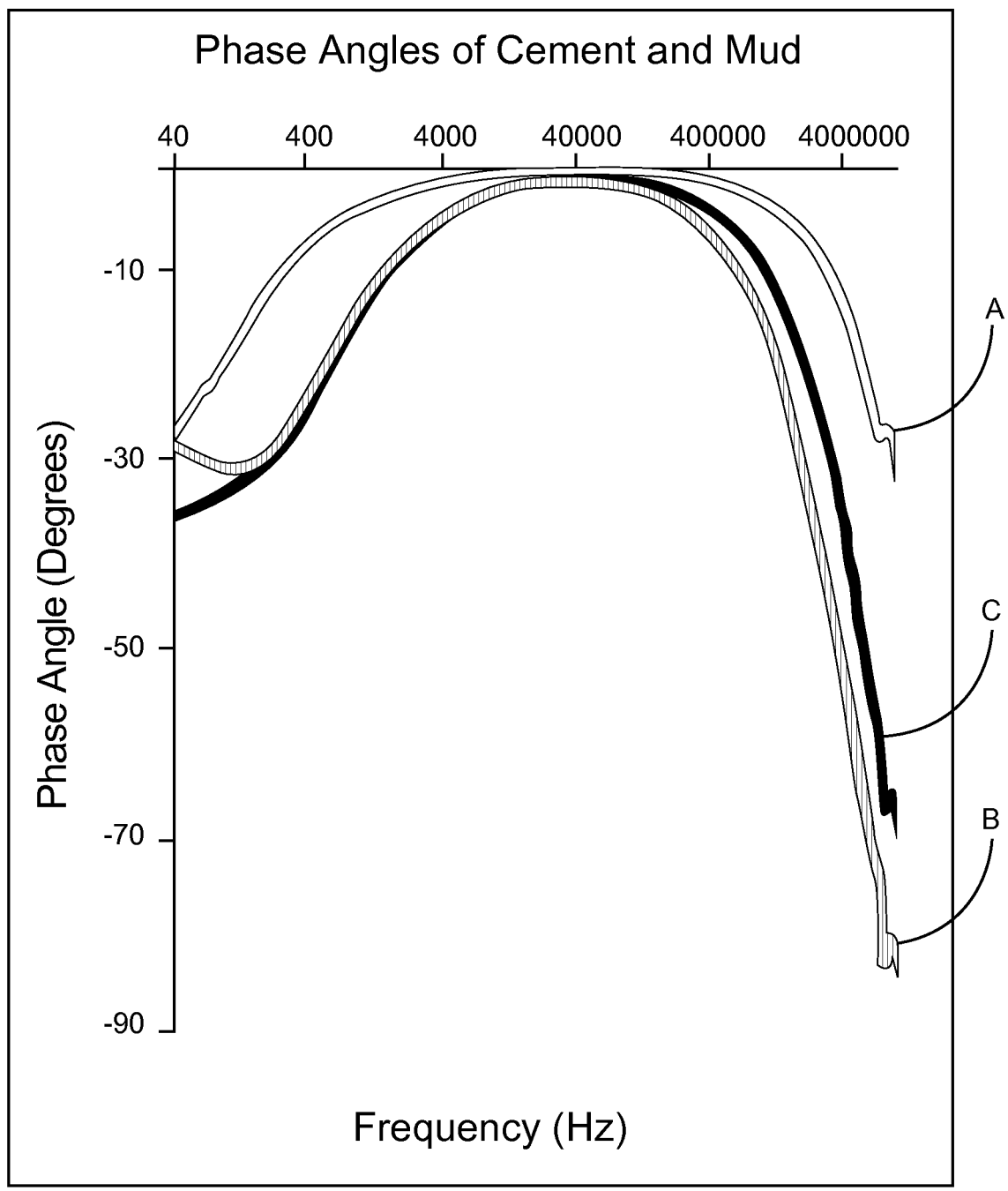
FIG. 14 illustrates example phase angle fingerprints for cement, drilling mud and contaminated cement measured in accordance with some embodiments.

FIG. 14 illustrates example phase angle fingerprints for cement (curve A), a drilling mud such as Performadril mud (curve B) and contaminated cement (curve C) measured in accordance with some embodiments. As will be noted, the phase angle fingerprints are distinct from each other and therefore systems such as surface system 38 can distinguish mud, cement, and contaminated cement using the phase angle fingerprints measured or calculated in accordance with some embodiments described earlier herein.

Systems and Methods for Fluid Discrimination Using Impedance Spectra

As describe above regarding FIGS. 1-14, a system such as surface system 38 (FIG. 1) can use AC IS to capture impedance measurements and to generate and analyze Nyquist plots. As described earlier herein regarding FIG. 7, the bulk resistance $R_b$ of cement increases as the cement hydrates. The tortuosity and connectivity of the cement pore structure increases overtime causing an increase in the bulk resistance $R_b$ of the cement. Systems, for example surface system 38 (FIG. 1), can predict the permeability and diffusivity of the cement through use of the measurements for bulk resistance. Furthermore, systems can distinguish cement from other fluids, and systems can detect cement contamination, using impedance spectra or data related to impedance spectra that has been captured and saved to data storage as described earlier herein. The surface system 38 can receive impedance measurements for analysis from fluid sensing components that the operator has mounted to the casing 20 when the casing 20 is placed downhole.

Figure 15:
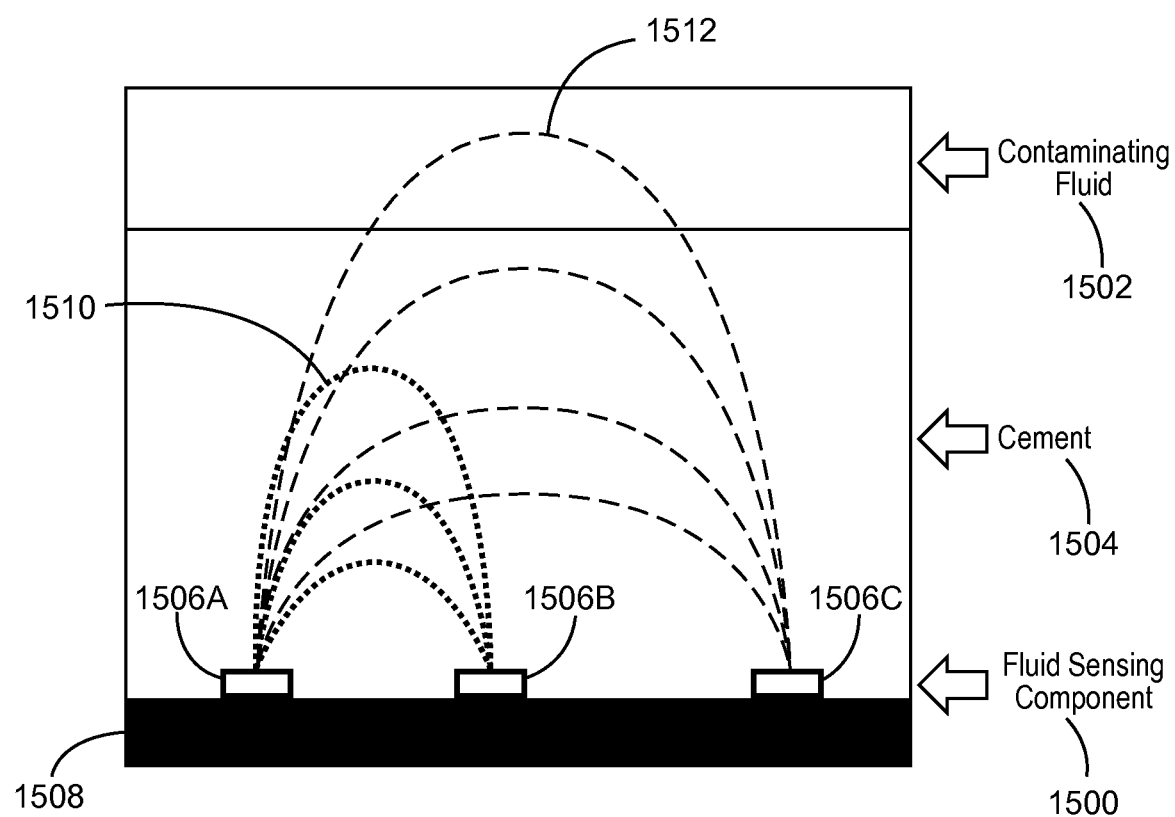
FIG. 15 depicts a side view of an example fluid sensing component as can be used to measure impedance spectra in accordance with some embodiments.

FIG. 15 depicts a side view of an example fluid sensing component 1500 as can be used to measure the cement (or other well-servicing fluids(s)) present within annulus 26 by measuring electrical impedance in accordance with some embodiments when the fluid sensing component 1500 is included on a communication assembly or casing 20 portion placed downhole.

Fluid sensing component 1500 includes electrodes 1506A-C mounted on an insulating base 1508 to prevent shorts against metallic surfaces, such as the body member of a communication assembly (as described below, referring to FIGS. 20-21 or a supporting section of casing 20 (FIG. 1). Materials including Protech DRB™ material or Protech CRB™ material, available from the Halliburton Company of Houston, Tex. can provide a suitable insulating base 1508. Electrodes 1506A-C can be placed on insulating base 1508 in various shapes, such as conductive strips, concentric loops etc. Each electrode 1506A-C can be in the form of a solid component (for example, metal plates or strips) secured to insulating base 1508, or, in other examples, can be formed of a coating metallized, or otherwise deposited, onto insulating base 1508.

In various example systems, structures and methodologies as described herein can provide variable depth sensing of a contaminating fluid 1502 in contact with set oil well cement 1504 but not in contact with the fluid sensing component 1500 itself. The spacing of electrodes 1506A-C of fluid sensing component 1500 allows for the variable depth of penetration of electric field lines. For example, electric field lines 1510, generated between electrodes 1506A and 1506B by providing excitation signals to one of electrodes 1506A and 1506B, may penetrate only into cement 1504. In contrast, electric field lines 1512, generated between electrodes 1506A and 1506C by providing excitation signals to one of electrodes 1506A and 1506C, may penetrate further into cement layer and, in some cases, into contaminating fluid 1502.

The relative placement, geometric configuration, and other design parameters of electrodes 1506A-C can be adjusted to improve the likelihood of detection of changes in the dielectric environment resulting from changes in the surrounding fluids. For example, the electrodes 1506A-C can be positioned nearer to each other for greater sensitivity to changes nearer to fluid sensing component 1500. Conversely, electrodes 1506A-C can be positioned further away from each other for greater sensitivity to changes further away from fluid sensing component 1500. In some embodiments, electrodes 1506A-C can be spaced from each other in a symmetrical arrangement, for example, electrode 1506A can be spaced at about a same distance from electrode 1506B as electrode 1506C is spaced from electrode 1506B. In other embodiments, electrodes 1506A-C can be spaced asymmetrically from each other. For example, electrode 1506A can be spaced about ½ inch from electrode 1506B and electrode 1506B can be spaced about one inch from electrode 1506C. Embodiments are not limited to any particular spacing, however. Operators can determine appropriate electrode spacing to provide comparative measurements of impedance at various distances from a communication assembly. Electrode spacing can also be determined based on, for example, power requirements, expected types of substances and fluids downhole, and surface areas of electrodes 1506A-C, among other factors.

In some embodiments, fluid sensing component 1500 can include two or more electrodes arranged as parallel plates, similarly to the parallel plates described earlier herein regarding FIG. 3. In at least these embodiments, the parallel plates can be separated using a spacer, and the space between the parallel plates can include a ceramic or resin material.

In some embodiments, electrodes 1506A-C will be directly exposed to the surrounding environment, for example to cement 1504 as can be present in annulus 26 (FIG. 1). In at least these embodiments, electrodes 1506A-C will be in direct contact with cement 1504 or any other fluids in annulus 26. In at least those embodiments for which electrodes 1506A-C are in direct contact with wellbore fluids, electrodes 1506A-C may couple galvanically or capacitively with fluids in the annulus. In embodiments for which electrodes 1506A-C couple galvanically with fluids in the annulus, electrodes 1506A-C can include a corrosion resistant metal (e.g., stainless steel) to reduce or eliminate the possibility that electrodes 1506A-C generate corrosion-related defects in the cement during the monitoring period.

In embodiments for which electrodes 1506A-C couple capacitively with fluids in the annulus, electrodes 1506A-C can include a metal (e.g., titanium). In some situations, the metal can oxidize to form a thin self-healing, electrically insulating, chemically inert, abrasive resistant chemical barrier (e.g., titanium oxide) for improved reliability of electrodes.

In other embodiments, a protective layer (not shown in FIG. 15) can be disposed over electrodes 1506A, 1506B, 1506C to insulate them from well fluids and to provide abrasive resistance for electrodes 1506A, 1506B, 1506C. This barrier can include a ceramic or epoxy resin. In at least these embodiments, electrodes 1506A, 1506B, 1506C will not be in direct contact with the fluids. In at least these embodiments, electrodes 1506A, 1506B, 1506C will couple capacitively with the fluids.

In order to generate impedance spectra similar to those described above as being generated in a laboratory environment, one or more of the electrodes 1506A-C(e.g., an "injection electrode") can receive a series of excitation signals in a frequency sweep including relatively low frequencies, for example in a range of about 40 Hz to 10 MHz. A signal generator (such as VCO 1832, FIG. 18) can provide these series of excitation signals. In response, the injection electrode will inject current into the surrounding environment, such as into cement 1504 (as an example fluid) or further into the surrounding environment, such as into contaminating fluid 1502. One or more other electrodes 1506A-C(e.g., a "receiving electrode") can receive the injected current. A processor or other system, for example, surface system 38, or another processor, can calculate impedance spectra to generate Nyquist plots, phase angle fingerprints, etc., as described earlier regarding FIGS. 1-14, and Equations (3)-(4).

Figure 16:
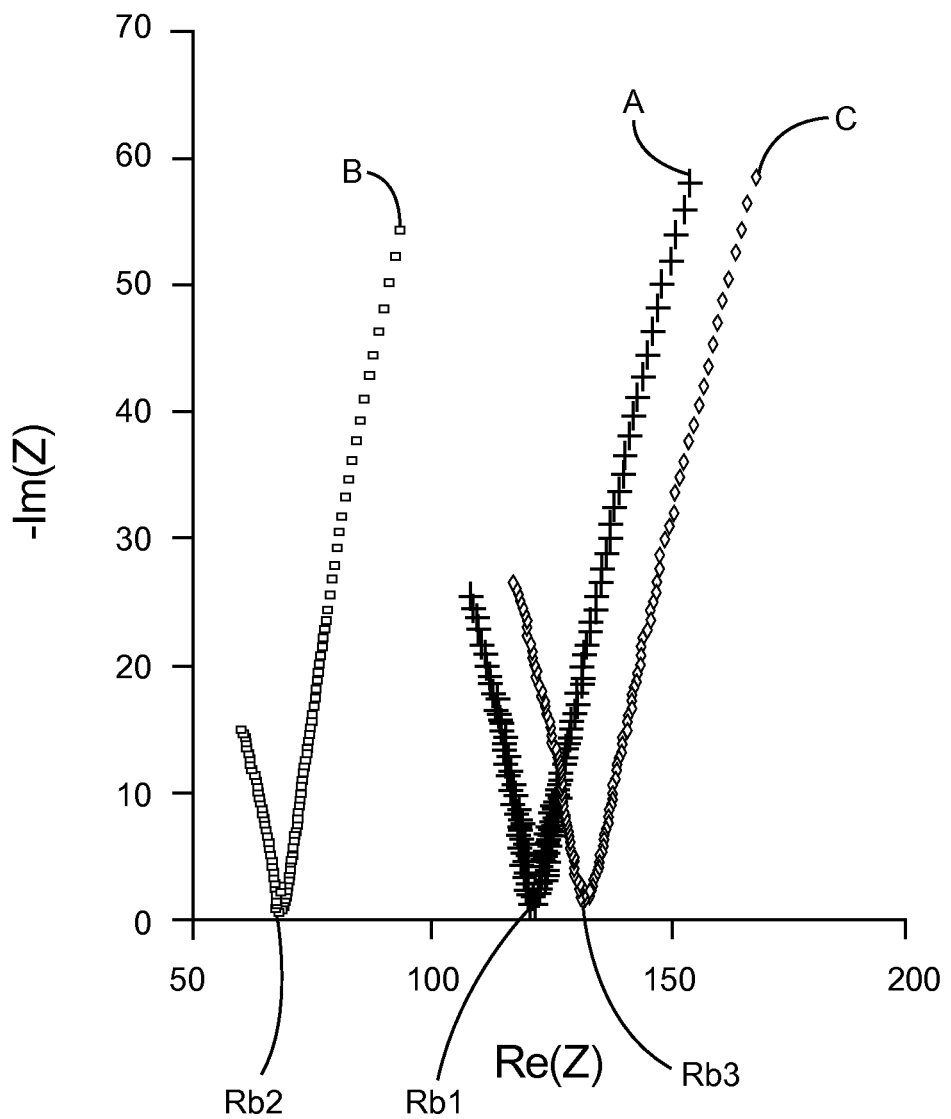
FIG. 16 illustrates example AC impedance spectra generated based an impedance response between a first pair of electrodes in accordance with some embodiments.

FIG. 16 illustrates example AC impedance spectra generated based on an impedance response between electrodes 1506A and 1506C in accordance with various embodiments. Impedance spectra can be the same or substantially similar as impedance spectra described earlier herein regarding FIGS. 1-14. The example AC impedance spectra in FIG. 16 were generated by providing excitation signals at frequencies of 40 Hz to 4 MHz to an injection electrode such that injection currents passed through set cement, with a contaminating fluid layer including de-ionized water (curve A), 1.0 M potassium chloride solution (curve B), and an oil-based mud (curve C). However, impedance spectra can also be generated as described earlier herein using an unset cement slurry, or with no contamination of the set or unset cement, or with other contaminating fluids.

It will be appreciated by those of ordinary skill in the art that phase angle fingerprints, as described earlier herein regarding FIGS. 8-9 and 13-14, can be calculated or otherwise generated for further analysis and fluid discrimination functionalities.

As will be appreciated upon examination of FIG. 16, electrodes 1506A and 1506C will sense different values for characteristics of impedance spectra when different contaminating fluids impinge on cement. For example, bulk resistance Rb1 can be detected when the contaminating layer is de-ionized water, Rb2 can be detected when the contaminating layer is 1.0 M potassium chloride solution, and bulk resistance Rb3 can be detected when the contaminating layer is oil-based mud. Even though electrodes 1506A and 1506C were not in direct contact with the respective contaminating fluids, the bulk resistance measured changed as a function of the conductivity of the contaminating fluid layer.

Figure 17:
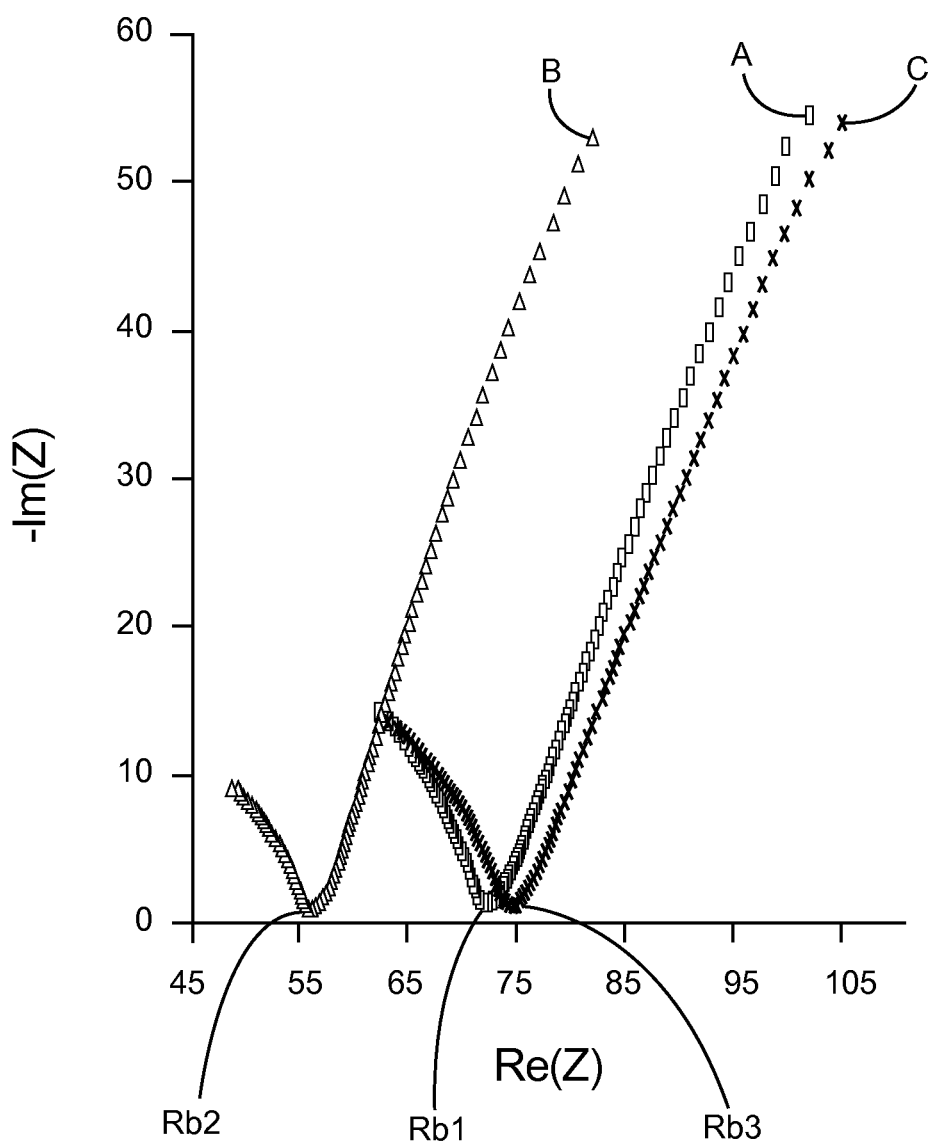
FIG. 17 illustrates example AC impedance spectra generated based on an impedance response between a second pair of electrodes in accordance with some embodiments.

FIG. 17 illustrates example AC impedance spectra generated based on an impedance response between electrodes 1506A and 1506B in accordance with various embodiments. Impedance spectra can be the same or substantially similar as impedance spectra described earlier herein regarding FIGS. 1-14. Similarly to the example AC impedance spectra of FIG. 16, the example AC impedance spectra in FIG. 17 were generated by providing excitation signals at a frequencies of 40 Hz to 4 MHz to an injection electrode. In response, injection currents were passed through set cement with a contaminating fluid layer including de-ionized water (curve A), 1.0 M potassium chloride solution (curve B), and an oil-based mud (curve C). However, impedance spectra can also be generated as described earlier herein using an unset cement slurry, or with no contamination of the set or unset cement, or with other contaminating fluids.

Similarly to FIG. 16, electrodes 1506A and 1506B will sense different impedances when different contaminating fluids impinge on cement. For example, bulk resistance Rb1 can be detected when the contaminating layer is de-ionized water, Rb2 can be detected when the contaminating layer is 1.0 M potassium chloride solution, and bulk resistance Rb3 can be detected when the contaminating layer is oil-based mud. Even though electrodes 1506A and 1506B were not in direct contact with the respective contaminating fluids, the bulk resistance measured changed as a function of the conductivity of the contaminating fluid layer.

However, it will be noted upon comparing FIG. 16 and FIG. 17 that electrodes 1506A and 1506C generate different impedance spectra than electrodes 1506A and 1506B. In particular, the electrode pair 1506A and 1506C (FIG. 16) gave greater resolution in the differences between the contaminating fluid layers, due at least in part to the greater penetration of the electric field lines 1510 caused by the greater distance between electrodes 1506A and 1506C, as depicted in FIG. 15.

Accordingly, embodiments implementing fluid sensing components 1500 provide the ability to sense the distance of a contaminating fluid layer from the electrode pair 1506A and 1506C and from the electrode 1506A and 1506B. Embodiments may be capable of sensing contaminating fluid layers at distances of 12 to 18 inches from the fluid sensing components 1500. Further due to this capability, structures and methodologies as described herein can diagnosis breaches in cement integrity by detecting contaminating fluids 1502.

Figure 18:
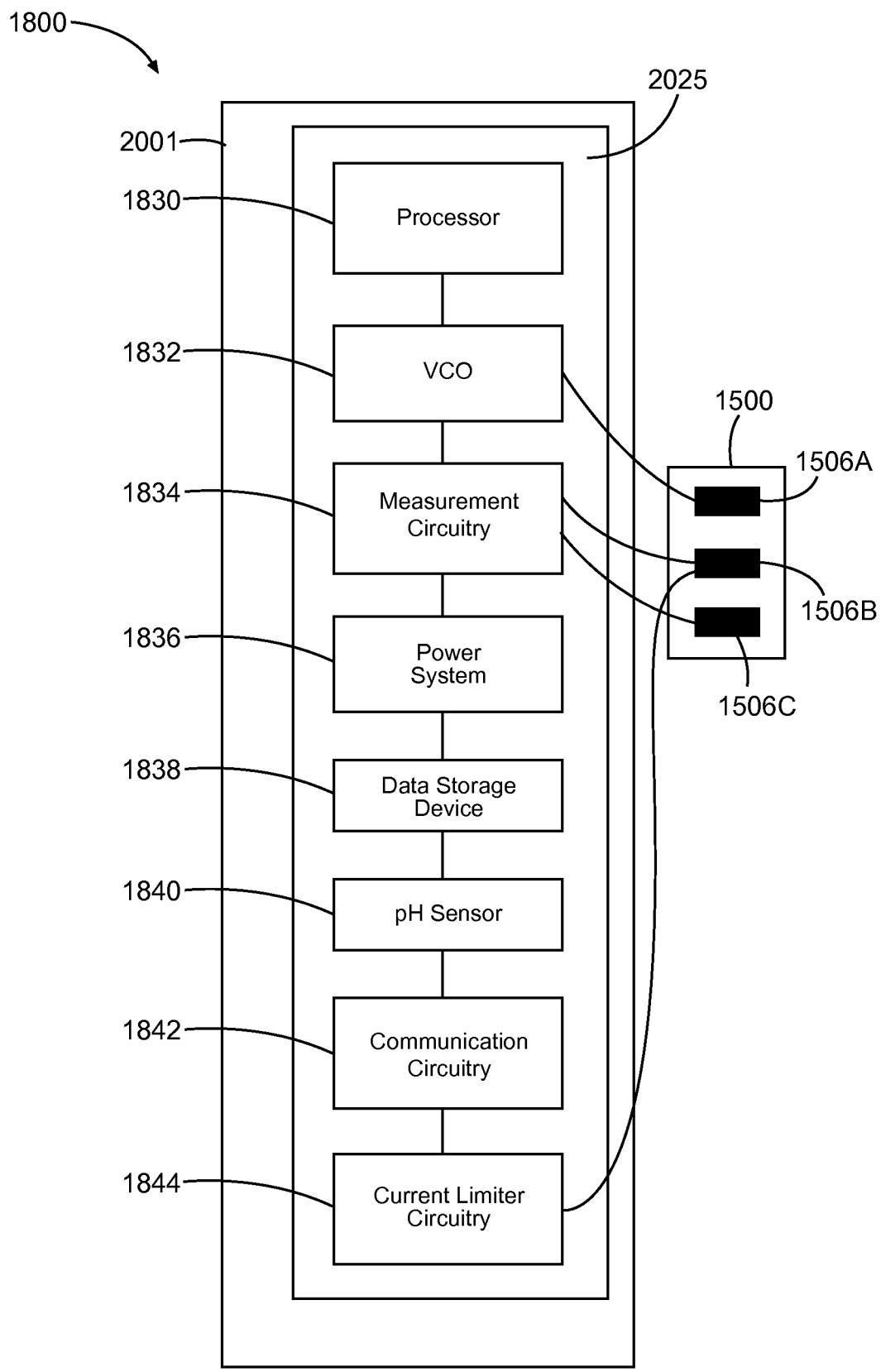
FIG. 18 depicts a schematic view of an example electronics assembly for performing functions of various embodiments.

FIG. 18 depicts a schematic view of an example electronics assembly 1800 that will perform functions of various embodiments. Electronics assembly 1800 provides excitation signals as described regarding FIGS. 15-17, and electronics assembly 1800 measures voltages and currents such as those described with reference to Equations (1) and (2) for use in calculating impedance spectra as described with reference to Equations (3)-(4) and FIGS. 6-14.

In various embodiments, one or more components of electronics assembly 1800 shown in FIG. 18 will be housed in rib 2001 or tube 2025 in a communication assembly (discussed later herein in reference to 2000 in FIG. 20). In the depicted example of electronics assembly 1800, the assembly includes one or more processors 1830 and a variable frequency generator to provide excitation signals to one or more of electrodes 1506A-C. In this example, the variable frequency generator is a voltage-controlled oscillator (VCO) 1832; but other forms of generators may provide the excitation signals, such as a dedicated integrated circuit (IC) and related circuitry.

Measurement circuitry 1834 couples to one or more of electrodes 1506A-C, to receive measure electrical parameters such as voltage and current resulting from passage of the excitation signals through the fluid and other materials in the well annulus 26.

Processor(s) 1830 control the operation of VCO 1832 and of measurement circuitry 1834. For example, processor(s) 1830 can control VCO 1832 according to properties of the fluid in the borehole, the amount of time that has elapsed since the fluid was placed in the borehole, etc. Processor(s) 1830 additionally process received signals, as described elsewhere herein, such as in reference to FIG. 19. In some example systems, one or more processors may be dedicated to the functionality associated with measurement circuitry 1834. Where electronics assembly 1800 does all processing, each fluid-sensing component 1500 will typically consist primarily of a plurality of electrodes in electrical communication with electronics assembly 1800, with all other functionality provided by electronics assembly 1800.

Any one or more processors 1830 and/or measurement circuitry 1834 will typically be coupled to a data storage device 1838 for either temporary or continued storage of instructions, data, etc. Other components of electronics assembly 1800 can couple to the data storage device 1838 as desired for a specific implementation. The data storage device 1838 may be any form of electrical storage mechanism, and in most examples will include one or more of volatile or nonvolatile memory, including one or more of DRAM, SRAM, Flash, MRAM, and combinations of any of the foregoing, as well as other known forms of memory devices. For purposes of the present disclosure, any such storage mechanism, whether volatile or nonvolatile memory shall be considered a non-transitory storage device (or memory).

Electronics assembly 1800 also includes a power system 1836 configured to supply power at least in the electronics assembly 1800, and in many cases to the entire communication assembly (as discussed at 2000, in FIG. 20), with which it is associated. In many examples, power system 1836 will include one or more batteries. Power system 1836 may provide power, on the order of about 10 milliwatts to 200 milliwatts, for each iteration of series of excitation signals described below regarding FIG. 19. Processor 1830 can control power system 1836 to operate communication assembly for a time duration sufficient for monitoring fluids throughout, for example, a curing process. To provide enhanced power efficiencies, processor 1830 can awaken communication assembly 2000 from a sleep state based on, for example, a pH change detected by pH sensor 1840.

Example electronics assembly 1800 will often also include communication circuitry 1842 to enable communication with an external location, as described elsewhere herein. Electronics assembly 1800 can transmit, receive, process, and telemeter EM signals to a central processing unit located at the surfaces. Example electronics assembly 1800 will often also include current limiter circuitry 1844 to suppress currents from being injected from at least one electrode of electrodes 1506A-C.

Processor(s) 1830 will evaluate signals received at one of electrodes 1506A-C to generate an impedance spectrum representative of an impedance between electrodes 1506A-C. Processor(s) 1830 will then evaluate the fluid in the borehole annulus through use of the impedance spectrum to determine fluid identities, contamination, and other parameters or conditions based on calculations of impedance spectra described earlier herein regarding FIGS. 6-14.

Alternatively or in addition, the processor(s) 1830 can telemeter relevant measurements to a surface system 38 (FIG. 1) or other system so that the surface system 38 or other system can perform fluid identification, display impedance spectra, or otherwise process impedance measurements. For power-saving purposes, the processor(s) 1830 may refrain from telemetering at least some data. For example, if measured impedance spectra or fluid characteristics are within an expected range, the processor 1830 may refrain from telemetering data until these or other values fall outside an expected range.

Software, hardware, firmware, or any combination thereof can generate impedance spectra, perform fluid identification, or detect contamination based on impedance spectra.

Figure 19:
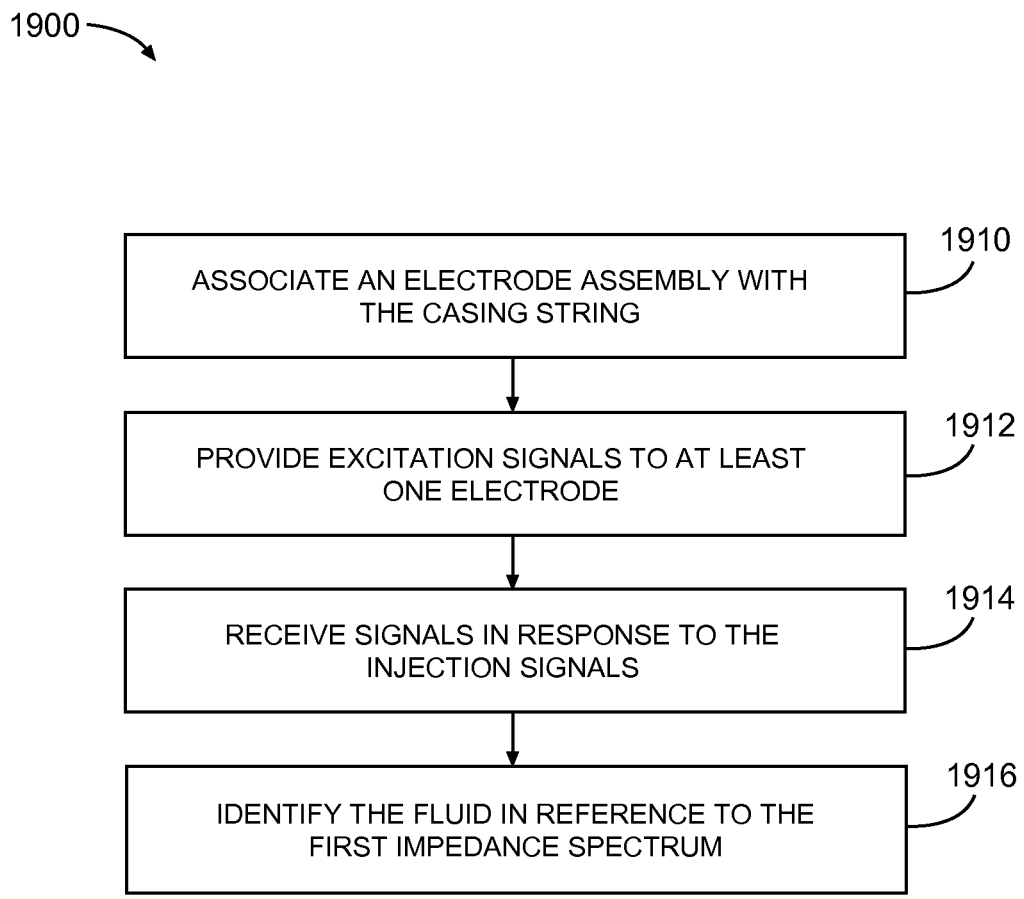
FIG. 19 depicts a flow chart of an example method for using electrodes of a fluid sensing component and components of an electronics assembly to perform impedance measurements in accordance with some embodiments.

FIG. 19 depicts a flow chart of an example method 1900 for using electrodes 1506A-C of fluid sensing component 1500 (FIG. 15) and components of electronics assembly 1800 to identify fluids or contamination of fluids using impedance spectra in accordance with some embodiments. Some operations of method 1900 may be implemented by surface system 38 (FIG. 1), processor 1830, measurement circuitry 1834 or other circuitry included in electronics assembly 1800 (FIG. 18) or by components such as communication components of communication assembly (as described at 2000 in FIG. 20).

In operation 1910, at least one fluid-sensing component 1500 is deployed on a casing 20. Fluid sensing component 1500 can be deployed with a communication assembly or separately from a communication assembly (as described at 2000 in FIG. 20). Fluid sensing component 1500 includes a plurality of electrodes 1506A-1506C in spaced relation to one another.

The example method 1900 continues at operation 1912, with providing, by VCO 1832, a first series of excitation signals at a first plurality of frequencies to at least one electrode of the plurality of electrodes to inject a first series of injection signals into fluid in the borehole annulus. The processor 1830, surface system 38, or other system can select a frequency range to be used for the first plurality of frequencies based on an expected identity of the fluid in the borehole annulus.

The example method 1900 continues at operation 1914 with receiving, by measurement circuitry 1834, signals in response to the first series of injection signals through at least one other electrode of the plurality of electrodes. The received signals will be representative of a first impedance spectrum including impedance values representative of the fluid in the borehole annulus as described earlier herein regarding Equations (1)-(4).

The example method 1900 continues at operation 1916 with identifying, by the processor 1830 or other system such as surface system 38, the fluid in reference to a characteristic of the first impedance spectrum. This characteristic can include the phase angle fingerprint as described earlier herein regarding FIGS. 8, 9, 13 and 14. The characteristic can also include bulk resistance values selected through examination of a Nyquist plot of the impedance spectrum, such as those described earlier herein regarding FIGS. 5A-B, 6, 7, 16, and 17.

The example method 1900 can be executed any number of times throughout the lifetime of a well when the VCO 1832 provides various series of excitation signals to the same or different electrodes 1506A-C. The VCO 1832 can use the same frequency ranges for each series of excitation signals that the VCO 1832 provides to electrodes 1506A-C. However, embodiments are not limited thereto, and the VCO 1832 can use different frequency ranges for one or more series of excitation signals. The VCO 1832, processor 1830, or other system can select the frequency range to be used for a particular series of excitation signals based on the actual or expected identity of the fluid, the amount of time that has passed since providing the previous series of excitation signals, the time since cement emplacement, the actual or expected hydration state of the fluid, or on any other factor or criterion. The frequencies to be used can be determined prior to the operations of method 1900, or in other alternatives, can be communicated from surface system 38 or other system, or can be determined by a downhole processor (1830 in FIG. 18).

The VCO 1832 can excite different electrodes 1506A-C for each series of excitation signals, such that an injecting electrode injects different sets of currents to different distances into the fluid in the borehole. When a receiving electrode receives response signals responsive to each of these sets of injected currents, the processor 1830 will generate different sets of impedance spectra, each responsive to respective series of excitation signals. The processor 1830 will therefore detect changes in characteristics in the fluid, as a function of distance from electrodes 1506A-C, through comparison of the characteristics of each set of impedance spectra. Any or all of these sets of impedance spectra, or data representative of the sets of impedance spectra, can be retrieved from or stored in local or remote data storage.

The processor 1830 or surface system 38 can initiate or trigger impedance spectra generation periodically throughout a hydration or "setting" period of emplaced cement, and the processor 1830 or other circuitry can later take further measurements to monitor cement quality. The processor 1830, surface system 38, or any other system can select the amount of time that should pass between each generation of impedance spectra based on the identity of the fluid at any given time, geographical considerations, an expected hydration state of the fluid, or any other consideration or criterion. The processor 1830 can compare each set of generated impedance spectra with any other set to monitor quality, hydration state, etc.

For example, processor 1830 or surface system 38 can determine fluid identities according to the predicted or estimated fluid resistivities that have been predicted or estimated based on physical measurements, e.g., at the well site, or in a laboratory. Processor 1830 or the surface system can access or retrieve data from a lookup table that defines fluid types of fluids within the annulus based on characteristics of impedance spectra, wherein the lookup table was previously generated based on laboratory measurements or field experiments, etc., such as those described above regarding FIGS. 2-14. By comparing obtained impedance spectra characteristics with these predicted or estimated characteristics, processor 1830 can detect presence (or absence) of a particular fluid to identify what fluids are present at the location of the electrodes, which may monitor, for example, of the cementing operation (for example, to determine the TOC).

In many examples, the measurements and/or the determined impedance spectra will be telemetered to surface system 38, which may be done essentially in real time or at selected intervals. Surface system 38 can use these measurements, after placement of the cement, to identify the cure state of the cement, and also during cure or at later intervals to identify any fluid incursion of the cement barrier. In examples in which the impedance spectra are either not determined downhole or are not implemented to determine a cement cure state downhole, such operations can be performed at the surface, for example by surface system 38.

In examples of the described method, surface system 38 can receive measurements from the communication assembly over a variety of time intervals and display layer boundaries, or another fluid parameter, as a function of time or frequency.

In some embodiments, processor 1830, surface system 38, or another system can model, invert, or provide display of the measured impedances to generate resistivity data of the materials filling annulus 26 between casing 20 and formation 14. In some embodiments, processor 1830, surface system 38, or another system can model, invert, or provide display of the measured impedances acquired to generate effective medium models of the materials filling annulus 26 between casing 20 and formation 14. These effective medium models can functionally describe measured impedances in terms of physical properties such as fluid, grain size, etc. In various embodiments, surface system 38 can apply methods of model parameterization and regularization to enhance this inversion or imaging.

In some example systems, the method may also be used to identify properties of formations 14 defining wellbore 18 in addition to, or in some examples instead of, properties of materials in annulus 26. In such methods, generation of excitation signals of a magnitude and frequency as to result in the current traversing a portion of formation 14 to reach a receiving electrode can be received and used to predict, calculate, or estimate formation 14 resistivity in the proximity of the injecting and receiving electrodes. In some cases, these determinations of formation 14 resistivity can be at least in part based upon or correlated with well logs acquired from open-hole wireline or logging-while-drilling (LWD) instruments. Surface system 38 can perform multiple deterministic-based inversions or stochastic-based inversions and subsequent post-inversion analyses that span different initial models, constraints, and regularization to quantify model uncertainty.

Figure 20:
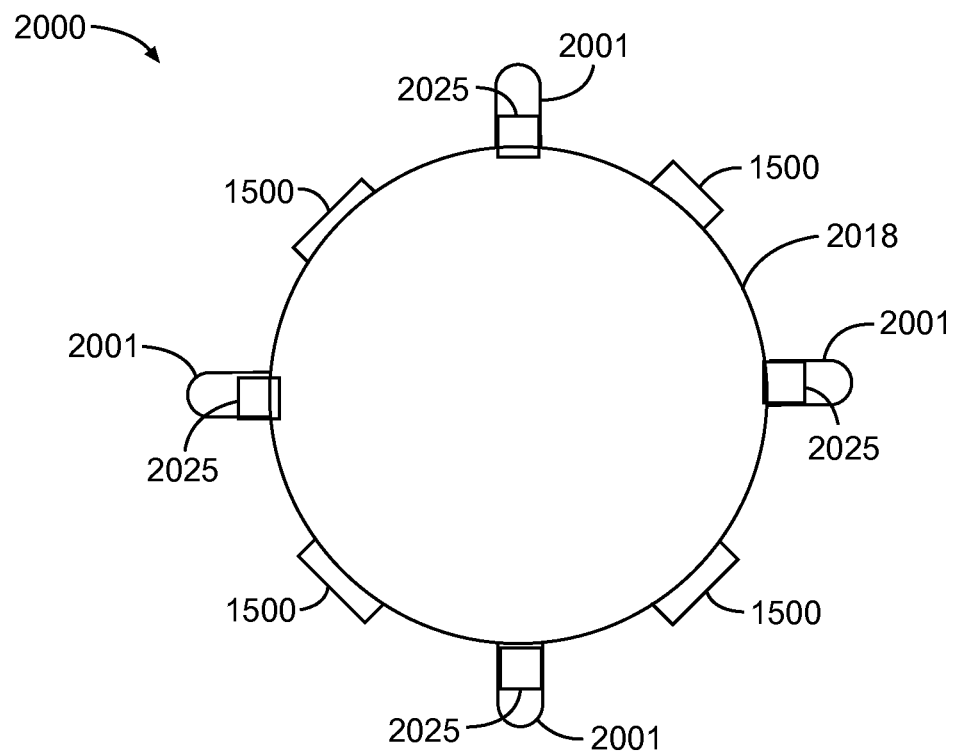
FIG. 20 depicts a cross-sectional schematic view of an example communication assembly as may be used to measure impedances in sealant (or other well servicing fluids) present within different azimuthal regions of the annulus in accordance with some embodiments.

FIG. 20 is a cross-sectional schematic view of an example communication assembly 2000 on which fluid sensing components 1500 and other components can be mounted to measure the sealant (or other well servicing fluids) present within different azimuthal regions of the annulus; or to measure or determine impedance, ion concentration, acidity, or other properties of fluids proximate communication assembly 2000 in accordance with some embodiments. Communication assembly 2000 is discussed below with reference to some elements depicted in FIG. 15.

Example communication assembly 2000 includes a plurality of ribs 2001 that extend longitudinally along communication assembly 2000 and in spaced relation to one another around the periphery of communication assembly 2000. Example communication assembly 2000 includes four ribs 2001 generally equally spaced around communication assembly 2000, and therefore generally equally spaced relative to the circumference of casing 20. As will be apparent to persons skilled in the art having the benefit of this disclosure, either a greater or a lesser number of ribs 2001 can be utilized according to needs of a particular application.

In communication assembly 2000, ribs 2001 are hollow, and house control circuitry and/or other electronics (1800 in FIG. 18), as well as additional circuitry to enable communications with an external location, etc. In many examples, ribs 2001 will be of a geometric shape that reduces or eliminates the effect of ribs 2001 on flow of fluids past or near ribs 2001. In many examples, ribs 2001 will encircle or enclose a tube 2025 or similar structure configured to house and protect control circuitry and other electronics therein from pressure, abrasion, etc. Such tubes 2025 or other structures can be include a suitable metal, such as steel, or another material suitable for the specific application, as will be apparent to persons skilled in the art having the benefit of this disclosure.

In various embodiments, communication assembly 2000 includes fluid sensing components 1500. As described herein with reference to FIGS. 15-19 and Equations (1)-(2), electrodes of fluid sensing components 1500 receives a series of excitation signals to inject a series of injection currents into the annulus 26. The injection currents can traverse the adjacent dielectric environment (i.e., the adjacent fluid) to reach one or more additional electrodes of fluid sensing components 1500.

In the depicted schematic representation, a fluid sensing component 1500 is provided between each pair of adjacent ribs 2001, such that a fluid sensing component 1500 is angularly offset from an adjacent fluid sensing component 1500, to provide impedance measurements that vary with properties of fluids passing by communication assembly 2000 in the well annulus 26. In other systems, a communication assembly may only include a single fluid sensing component 1500 proximate a given depth.

Depending on the number of fluid sensing components 1500 mounted to assembly 2000, fluid sensing components 1500 can be angularly offset from each other by a number of angular degrees, for example by about ninety degrees, about sixty degrees, etc. In the depicted example, fluid sensing components 1500 are presumed to be configured such that all electrodes of fluid sensing components 1500 are placed between ribs 2001. However, embodiments are not limited thereto and at least one electrode of a fluid sensing component 1500 can be mounted on a rib 2001 or in other configurations (as described below referring to FIG. 8). Further, in some embodiments, a fluid sensing component 1500 can be provided between one pair of adjacent ribs 2001, while a fluid sensing component 1500 may not be provided between another (or any other) pair of adjacent ribs 2001.

In some configurations, fluid sensing components 1500 can provide azimuthal information by detecting generally within a determined azimuthal region of annulus 26. In some implementations, these azimuthal regions may all be distinguished from one another, while in others the azimuthal regions may partially overlap with one another. The presence of overlap, or the degree of an overlap, if any, may depend on the number and placement of fluid sensing components 1500. Any number of ribs, tubes, or corresponding structures, may be provided as necessary to house the necessary circuitry, and as desired to provide detection within a determined azimuthal region surrounding communication assembly 2000 or to provide signaling and related processing for fluid sensing components 1500.

The various electronic circuits within each rib 2001 can communicate as desired with circuitry in another rib 2001. Such communications between can occur through use of any suitable mechanism as will be apparent to those skilled in the art, for example, through use of a serial peripheral interface (SPI), though embodiments are not limited thereto.

Communication assembly 2000 can associate with casing 20 by a variety of mechanisms. Each communication assembly includes a body member 2018 supporting other components and facilitating association with casing 20.

Figure 21:
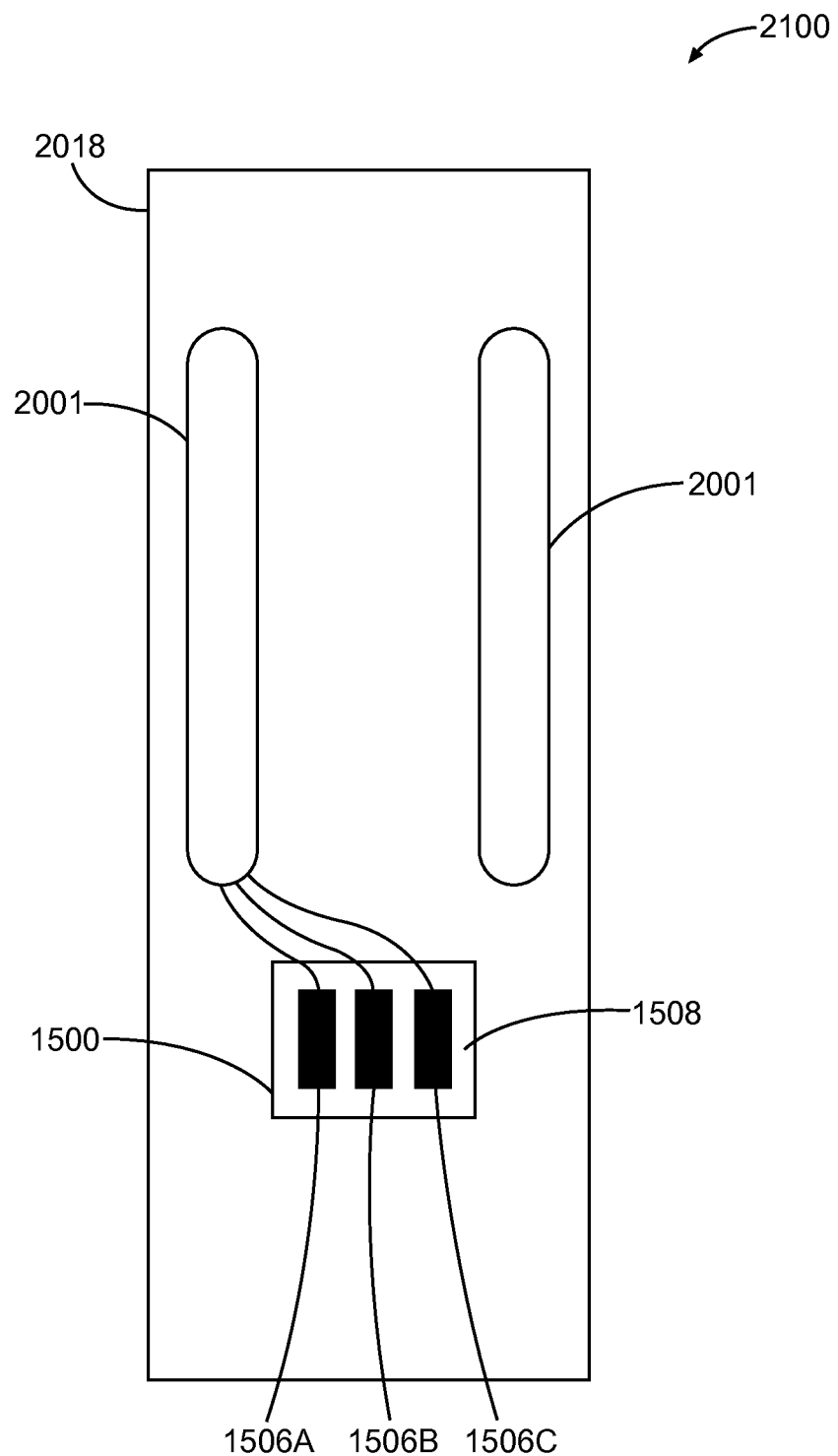
FIG. 21 depicts a side view of an example communication assembly in accordance with some embodiments.

FIG. 21 depicts a side view of a communication assembly 2100 in accordance with some embodiments. Components comparable to those discussed relative to FIGS. 15 and 20 are numbered similarly in FIG. 21.

Fluid sensing component 1500 includes a plurality of electrodes 1506A-C. Electrodes 1506A-C will be referred to as belonging to a fluid sensing component 1500 when one of the electrodes 1506A-C provides injection current received at another of the electrodes 1506A-C.

While FIG. 21 characterizes a system having three electrodes, other configurations may be used. Depending upon the specific materials of construction of various portions of a respective communication assembly, electrodes 1506A-C may be secured proximate a metallic surface, such as by being mounted on an insulating base 1508 to prevent electrical shorts against such metallic surface of the communication assemblies.

In the depicted example, communication assembly 2100 includes a plurality of electrodes 1506A-C arranged to provide a fluid sensing component 1500. Though only one side of communication assembly 2100 is shown, it should be understood that the described fluid sensing component 1500 might be replicated at a plurality of azimuthally offset locations around communication assembly 2100. Therefore, any fluid sensing component 1500 can sense fluid properties within an overlapping or non-overlapping azimuthal range of other fluid sensing components 1500 around communication assembly 820.

Persons skilled in the art having the benefit of this disclosure will recognize that the longer the spacing between an electrode 1506A-C injecting an injection current and an electrode 1506A-C configured to receive the injection current after the injection current has traversed the surrounding dielectric environment, the greater the distance the signal will extend into that environment. This effect can be further promoted with guard electrodes placed between the injecting and receiving electrodes, as known to persons skilled in the art. Additionally the longer distance allows the signals to better reflect the effects of that dielectric environment. In applications in which these effects are desired, the electrodes can be longitudinally spaced, one of above the other, along the communication assembly 2000. Electrodes 1506A-C can extend longitudinally along the assembly or laterally around the communication assembly.

As is apparent from the discussion above, in many example systems, a plurality of communication assemblies will be disposed in longitudinally spaced relation to each other along the casing 20, at least over a region of interest relative to either the sealing operation or to other downhole conditions. Accordingly, by sensing fluids of a certain type in response to detecting characteristics of impedance spectra using measured currents and voltages in accordance with Equations (1)-(4), a location, in particular TOC, can be determined by finding a location on casing 20 where below it, impedance spectra with a first characteristic of the sealant are identified, while above the location, only impedance spectra with a second characteristic associated with other fluids, for example spacer fluid or drilling mud, are identified. Furthermore, monitoring of quality of barrier, and fluid discrimination can be performed using apparatuses and methods in accordance with some embodiments.

Each communication assembly will preferably include an azimuthal indicator, for example a compass, to determine the orientation of the communication assembly once it is disposed within the borehole. With a known orientation of the communication assembly, the orientation of each rib or fluid sensing component 1500 will be known and therefore the quadrant or other azimuthally offset region being investigated will similarly be known. The depth of each casing assembly can be known, for example through a record of the location of each communication assembly as it is associated with casing 20 as the casing is placed in the wellbore, providing a measure of depth as to the surface.

In different examples, TOC measurement can be done after the pumping of the sealant is completed or the measurement can be a dynamic measurement of the TOC while the sealant is moving up annulus 26. The other measurements described herein facilitate measurements not only of the TOC, but also of the distribution of the cement or other sealant around the casing over the region of the casing string that includes associated communication assemblies. Identifying both the depth and orientation where this occurs facilitates remediation efforts.

Each communication assembly 2000 can report information associated with the fluid sensing components to a surface system, for example surface system 38, using communication methods known to those of ordinary skill in the art having benefit of this disclosure. In some examples, this may be as basic as a potential difference measurement associated with electrodes of a fluid sensing component, grouped, or formatted in a manner to indicate the azimuthal orientation of the sensing.

The novel techniques described above can determine properties of sealant (or another fluid in the borehole) by generating impedance spectra based on current and voltage measurements or other measurements taken by an electrode-based fluid-sensing component. As discussed earlier, signals, for example oscillating signals, can excite electrodes of the fluid sensing component. Processors or other associated electrical systems can enhance the sensitivity of the fluid sensing component by controlling which electrodes of the fluid sensing component will inject current into fluids, and by controlling which electrodes of the fluid sensing component will sense these injected currents, to inject electric field lines to different depths into cement or contaminating fluid layers.

In summary, using the apparatus, systems, and methods disclosed herein can provide azimuthally oriented indications of various properties or conditions downhole, and in particular can provide information regarding the top of cement and the quality of the barrier in of the annulus azimuthal regions. Properties of the annular fluid can similarly be monitored azimuthally, by determining impedance spectra characteristics based on impedances sensed by electrode-based fluid sensing components to infer dielectric properties of fluids.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Although specific embodiments have been illustrated and described herein, it should be appreciated that any arrangement configured to achieve the same purpose may be substituted for the specific embodiments shown. This disclosure is intended to cover any and all adaptations or variations of various embodiments. Combinations of the above embodiments, and other embodiments not described herein, will be apparent to those of skill in the art upon reviewing the above description.

What is claimed is:
1. A method for identifying fluids in a well, comprising:
associating a fluid sensing component with the exterior of a casing string, the casing string to be placed in a borehole in a subterranean formation to define an annulus between the casing and the subterranean formation, the fluid sensing component including a plurality of electrodes in spaced relation to one another;
after the casing string and associated fluid sensing component are in the borehole, providing a first series of excitation signals at a first plurality of frequencies to at least one electrode of the plurality of electrodes at a first time to inject a first series of injection signals into fluid in the annulus;
receiving signals in response to the first series of injection signals through at least one other electrode of the plurality of electrodes, the received signals representa- tive of a first impedance spectrum including impedance values representative of the fluid in the annulus;

identifying the fluid in reference to a characteristic of the first impedance spectrum;

at a second time, providing a second series of excitation signals at a second plurality of frequencies to at least one electrode of the plurality of electrodes to inject a second series of injection signals into fluid in the annulus, wherein a frequency range to be used for the second plurality of frequencies is based on at least one of the identity of the fluid at the first time, the time duration that has passed from the first time to the second time, and an expected hydration state of the fluid at the second time;

receiving signals in response to the second series of injection signals at an electrode that did not inject the second series of excitation signals, the second received signals representative of a second impedance spectrum including impedance values of the fluid in the annulus; and identifying a property of the fluid based on the second impedance spectrum.

2. The method of claim 1, further comprising: selecting a frequency range to be used for the first plurality of frequencies based on an expected identity of the fluid.

3. The method of claim 1, wherein the characteristic includes a phase angle fingerprint describing the fluid.

4. The method of claim 3, wherein the characteristic further includes a fluid bulk resistance value selected from within a Nyquist plot of the first impedance spectrum.

5. The method of claim 4, wherein the method further comprises identifying a hydration state of the fluid at the first time based on the bulk resistance value.

6. The method of claim 1, further comprising: selecting a time interval between the first time and the second time based on identification information of the fluid at the first time.

7. The method of claim 1, wherein the fluid is a hydrated sealant material, and wherein the method further comprises selecting a time interval between the first time and the second time based on an expected hydration state of the fluid in the borehole.

8. The method of claim 1, further comprising:

generating a message that includes fluid identification data if the fluid identification data is outside an expected range.

9. The method of claim 1, wherein the plurality of electrodes includes at least first, second, and third electrodes, each in unevenly spaced relation to one another, and the method comprises:

providing a first iteration of the first series of excitation signals to the first electrode;

subsequently providing a second iteration of the first series of excitation signals to the second electrode, to inject two sets of currents two different distances into the fluid in the borehole;

receiving first and second response signals responsive to the first and second iterations of excitation signals at the first and second electrodes, wherein the excitation signals traversed different distances into the annulus to reach the third electrode;

in response to receiving the first and second response signals, generating first and second impedance spectra, each responsive to a respective iteration of the excitation signals; and detecting a property of the annulus fluid through comparison of the characteristics of the first and second impedance spectra.

10. The method of claim 1, further comprising:

mixing a cement-based substance to form a cement slurry; and pumping the cement slurry down the inside of the casing string into the subterranean formation after the casing string and associated fluid sensing component are in the borehole.

11. The method of claim 10, further comprising:

monitoring a hydration state of the cement slurry.

12. A system, comprising:

a casing string, and a communication assembly supported by the casing string, the communication assembly comprising, a frequency generator, a plurality of electrodes, the frequency generator coupled to at least one of the plurality of electrodes, at least one processor, one or more memory devices in communication with the processor and containing instructions that, when executed by at least one processor, perform operations comprising, controlling the frequency generator to provide a series of excitation signals within a selected frequency range to at least one injection electrode to propagate into a surrounding annulus, receiving signals at a receiving electrode, the received signals resulting from the excitation signals, evaluating the received signals to generate an impedance spectrum representative of an impedance between the at least one injection electrode and the at least one receiving electrode, and evaluating the fluid in the surrounding annulus through use of the impedance spectrum;

data storage to store data representative of the impedance spectrum;

communication circuitry to telemeter the data; and wherein the processor is further configured to determine whether to telemeter the data responsive to determining whether the characteristic of the impedance spectrum indicates that fluid identification information is outside an expected range.

13. The system of claim 12, wherein the plurality of electrodes includes at least three electrodes, and the system further comprises current limiter circuitry to suppress currents from being injected from at least one electrode of the at least three electrodes.

14. The system of claim 12, further comprising a display to display the impedance spectrum, and wherein the impedance spectrum includes a Nyquist plot.

15. The system of claim 14, wherein the display is further configured to display phase angle fingerprints representative of the impedance spectrum.

16. An assembly, comprising:

a body member forming a portion of a casing string, the casing string to be placed in a borehole in a subterranean formation to define an annulus between the casing and the subterranean formation;

a fluid sensing component supported by the body member, the fluid sensing component including a plurality of electrodes, the fluid sensing component being arranged to sense an electrical impedance between one or more pairs of electrodes of the plurality of electrodes, wherein the electrical impedance varies based on properties of a fluid in the borehole; and an electronics assembly supported by the body member and operably coupled to the fluid sensing component, including, a frequency generator to provide a series of excitation signals to at least one injection electrode of the plurality of electrodes to cause the at least one injection electrode to inject a series of injection currents into the fluid in the borehole in response to determined criteria, measurement circuitry to receive signals resulting from the series of injection currents measure electrical properties of the fluid in the annulus, one or more processors, and one or more memory devices in communication with the processor and containing instructions that, when executed by one or more processors, cause the performing of operations comprising, determining criteria to control operation of the frequency generator, wherein the criteria include at least one of, a property of the fluid in the borehole, and an amount of time that has elapsed since the fluid was placed in the borehole, and generating an impedance spectrum based on the electrical properties measured by the measurement circuitry.

17. The assembly of claim 16, wherein the processor is further configured to control which of the plurality of electrodes the frequency generator is to provide with the excitation signals based on criteria, the criteria including one or more of an expected identity of the fluid in the borehole, a hydration state of the fluid in the borehole, and the time that has elapsed since the fluid was placed in the borehole.

18. The assembly of claim 16, wherein the assembly further comprises:

a data storage device configured to store measurements obtained by the measurement circuitry and to further store data representative of the impedance spectrum.

19. The assembly of claim 16, wherein the plurality of electrodes includes three electrodes, the three electrodes including a first electrode, a second electrode, and a third electrode, wherein at least at a selected time, the first electrode will be the injection electrode, and wherein the second and third electrodes are located at different spacings from the first electrode.

20. The assembly of claim 19, further comprising current limiter circuitry, and wherein the processor is further configured to control the current limiter circuitry to limit current injected by one of the first electrode, the second electrode, and the third electrode.

* * * * *